(12) United States Patent
Tan

(10) Patent No.: US 10,117,776 B2
(45) Date of Patent: Nov. 6, 2018

(54) DEVICES AND METHODS FOR TREATMENT OF OCULAR DISORDERS THROUGH DELIVERY OF THERAPEUTIC NUCLEIC ACIDS

(71) Applicant: DOHENY EYE INSTITUTE, Los Angeles, CA (US)

(72) Inventor: Chee Hian Tan, San Marino, CA (US)

(73) Assignee: DOHENY EYE INSTITUTE, Los Angeles, CA (US)

( * ) Notice: Subject to any disclaimer, the term of this patent is extended or adjusted under 35 U.S.C. 154(b) by 67 days.

(21) Appl. No.: 15/335,324

(22) Filed: Oct. 26, 2016

(65) Prior Publication Data

US 2017/0119580 A1    May 4, 2017

Related U.S. Application Data

(60) Provisional application No. 62/249,143, filed on Oct. 30, 2015.

(51) Int. Cl.

| | | |
|---|---|---|
| *A61N 1/30* | (2006.01) | |
| *A61F 9/007* | (2006.01) | |
| *A61F 9/00* | (2006.01) | |
| *A61B 3/16* | (2006.01) | |
| *A61K 9/00* | (2006.01) | |
| *A61K 31/713* | (2006.01) | |
| *A61K 41/00* | (2006.01) | |

(Continued)

(52) U.S. Cl.
CPC ............ *A61F 9/00781* (2013.01); *A61B 3/16* (2013.01); *A61F 9/0017* (2013.01); *A61F 9/0026* (2013.01); *A61K 9/0048* (2013.01); *A61K 31/713* (2013.01); *A61K 41/0047* (2013.01); *A61N 1/0472* (2013.01); *A61N 1/08* (2013.01); *A61N 1/32* (2013.01)

(58) Field of Classification Search
CPC ... A61F 9/0008; A61F 9/0026; A61N 1/0448; A61N 1/044; A61N 1/0543; A61N 1/36046; A61M 2210/0612
See application file for complete search history.

(56) References Cited

U.S. PATENT DOCUMENTS 4,109,653 A    8/1978  Kozam et al.
4,381,778 A    5/1983  Kozam et al.
(Continued)

FOREIGN PATENT DOCUMENTS

EP    2266656 A2    12/2010

OTHER PUBLICATIONS

International Search Report and Written Opinion dated Jan. 17, 2017 for International Application No. PCT/US2016/058949, in 18 pages.

(Continued)

*Primary Examiner* — Emily Schmidt
(74) *Attorney, Agent, or Firm* — Knobbe Martens Olson & Bear, LLP

(57) ABSTRACT

Several embodiments disclosed herein relate to the delivery of therapeutic nucleic acids to an ocular tissue in order to provide a therapeutic effect to reduce symptoms of or otherwise alleviate an ocular disorder. In particular embodiments, plasmid DNA is delivered to the cells of the trabecular meshwork in order to ameliorate increasing intraocular pressure. Devices and systems to accomplish this delivery are also disclosed.

23 Claims, 27 Drawing Sheets

(51) Int. Cl.
*A61N 1/04* (2006.01)
*A61N 1/08* (2006.01)
*A61N 1/32* (2006.01)

(56) References Cited

U.S. PATENT DOCUMENTS

| | | |
|---|---|---|
| 2004/0193097 A1 | 9/2004 | Hofmann et al. |
| 2007/0129693 A1* | 6/2007 | Hunter .................. A61F 9/0017 604/294 |
| 2007/0282405 A1* | 12/2007 | Wong, Jr. .................. A61F 7/12 607/104 |
| 2008/0183123 A1* | 7/2008 | Behar-Cohen ......... A61N 1/327 604/21 |
| 2012/0078162 A1* | 3/2012 | Gibson ................ A61N 1/0424 604/21 |
| 2014/0309613 A1 | 10/2014 | Behar-Cohen et al. |

OTHER PUBLICATIONS

Liu, Xuyang et al., Gene therapy targeting glaucoma: where are we?, Survey of Ophthalmology, 2009, vol. 54, Issue 4, pp. 472-486. See pp. 472-482.

Fan, Bao Jian et al., DNA sequence variants in the LOXL1 gene are associated with pseudoexfoliation glaucoma in a U.S. clinic-based population with broad ethnic diversity, BMC Medical Genetics, 2008, vol. 9, No. 1, 1 (internal pp. 1-7). See pp. 1-6.

\* cited by examiner

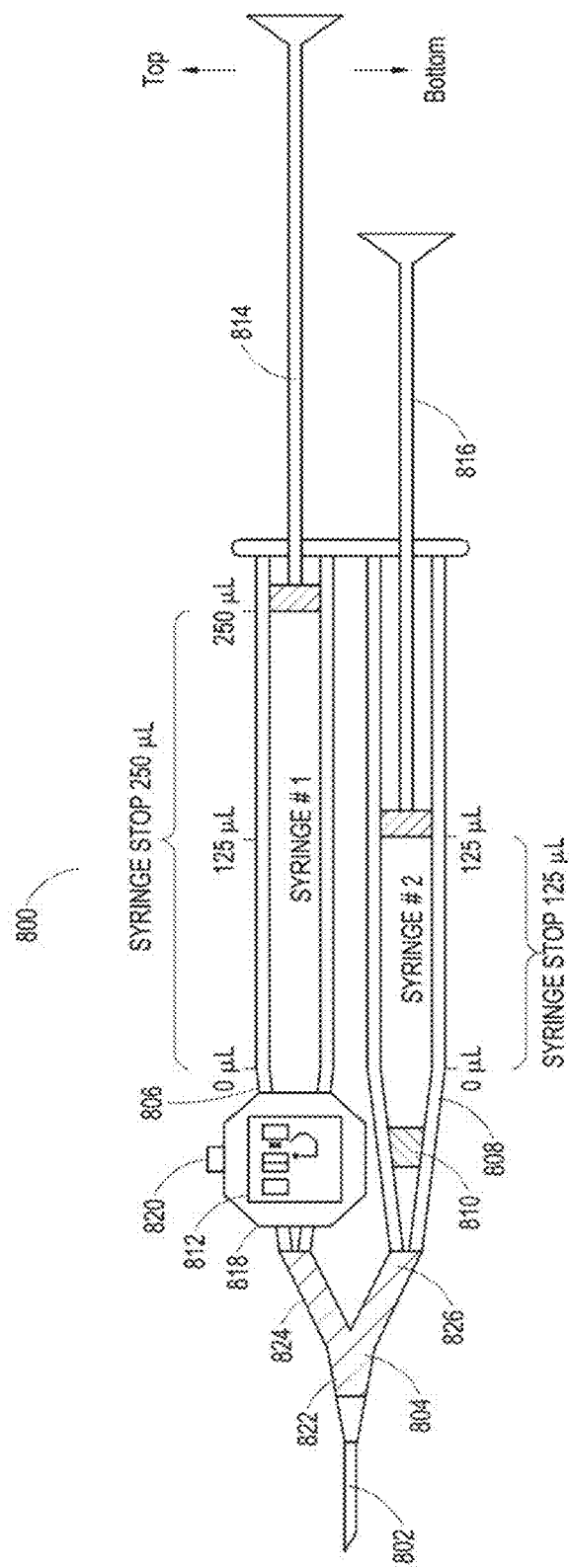

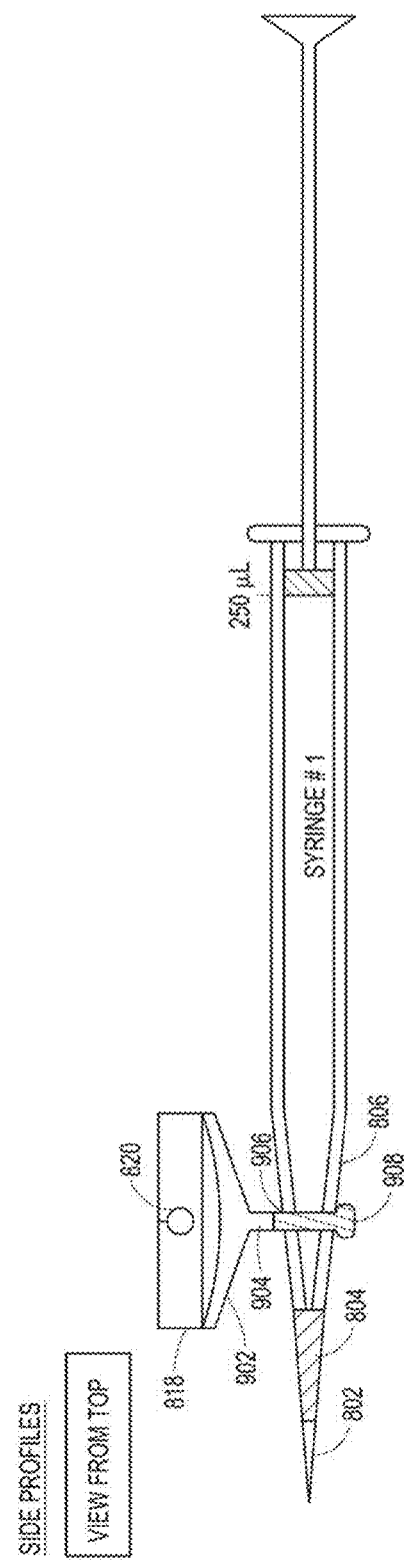

DEVICES AND METHODS FOR TREATMENT OF OCULAR DISORDERS THROUGH DELIVERY OF THERAPEUTIC NUCLEIC ACIDS

RELATED CASES

This application claims the benefit of U.S. Provisional Patent Application No. 62/249,143, filed on Oct. 30, 2015, the entire contents of which is incorporated by reference herein.

BACKGROUND

Field

Several embodiments of the present disclosure generally relate to eye treatment systems, and more particularly to systems, devices, and methods for treatment of ocular disorders through the delivery of therapeutic nucleic acids.

Description of the Related Art

As many ocular disorders remain incurable, it is important to develop technology systems for treating such disorders. For example, glaucoma is an ocular disorder that destroys retinal ganglion cells and their axons causing a corresponding loss of vision. Elevated intraocular pressure, either through increased production or decreased outflow of aqueous humor, is associated with glaucoma. The elevation in intraocular pressure can be caused, for example, by abnormal trabecular meshwork or to damage of the meshwork due to injury or disease of the iris, among other causes.

In general, doctors employ various tactics to help assist with treating ocular disorders, such as eye drops, medication, and surgery. However, patients who use eye drops and/or medication for treatment may experience several unwanted and/or unintended discomfort or other side effects. Additionally, even with surgery, doctors may not be able to efficiently control eye disease. After typical surgery, patients may also face several complications and risks, such as eye pressure that is too high or low, inflammation, discomfort, and/or scarring. In many chronic eye disorders, treatment seeks only to arrest disease progression rather than reverse underlying pathogenesis due to factors such as abnormal genes or proteins.

SUMMARY

In view of the need for treatments for various ocular disorders that are associated with and/or cause elevated intraocular pressure, there are provided herein various methods, devices, systems and kits for regulating intraocular pressure to a physiologic (or closer to physiologic) level.

In several embodiments, there is provided a device for generating and applying an electrical field to an ocular target tissue, comprising a first arcuate housing in which is positioned at least one positive electrode, a second arcuate housing in which is positioned at least one negative electrode. In several embodiments, the first and second arcuate housings are adjustable with respect to one another to yield an ovoid shape of a desired dimension, said desired dimension corresponding to the shape of an outer surface of an eye of a subject.

In several embodiments, the first and/or second arcuate housing comprise a plurality of positive or negative electrodes (respectively). In several embodiments, the device further comprises a control module configured to accept user input related to a percentage of the plurality of positive and negative electrodes to be activated during the application of the electrical field to a specific ocular target tissue. In several embodiments, the plurality of positive and plurality of negative electrodes are equal in number.

In several embodiments, the device comprises an injection system for delivery of a therapeutic agent to a specific ocular target tissue for the treatment of elevated intraocular pressure. In several embodiments, the injection system comprises at least a first syringe configured to deliver a therapeutic agent to an anterior chamber of the eye of the subject; and at least a second syringe configured to withdraw aqueous humor from the anterior chamber of the eye of the subject. Depending on the embodiment, syringes need not be used, but other devices suitable for delivery of a therapeutic agent can be used (e.g., a needle or other injection device in fluid communication with a source of therapeutic agent and a source of pressure or momentum causing the delivery of the therapeutic agent).

In some embodiments, the device comprises one or more pressure transducers configured to assess an intraocular pressure of the anterior chamber. In some embodiments, the device includes a control module or other logic to select and/or adjust one or more of a volume, a concentration, a rate, a frequency, or a pressure of the delivery of the therapeutic agent based on the assessed intraocular pressure.

In several embodiments, the device is configured to apply an electrical field focused on the trabecular meshwork of the eye of the subject. In additional embodiments the device is configured to apply an electrical field focused on the ciliary body of the eye of the subject.

In some embodiments, the ocular target tissue is the trabecular meshwork and the electrical field is applied at a voltage between 100 mV and 100 V, wherein the electric field is pulsed between 1 and 20 pulses, wherein the pulses are applied for a duration of between 0.5 and 10 milliseconds per pulse, and wherein the pulses are separated by an interval of between about 20 to 150 milliseconds.

In several embodiments, the device is configured to deliver the therapeutic agent in a volume of about 10 to about 1000 microliters, and at a concentration between about 10 micrograms nucleic acid per milliliter to 5000 micrograms per milliliter.

In several embodiments, the volume of aqueous humor withdrawn is equivalent to the volume of therapeutic agent delivered, and the withdrawal of aqueous humor is performed prior to delivery of the therapeutic agent. However, in additional embodiments, the volume of aqueous humor withdrawn may be greater or less than the amount of therapeutic agent delivered. Likewise, the delivery of the therapeutic agent and withdrawal of aqueous humor can be performed in any order, including alternating segments (e.g., delivery, withdrawal, delivery, etc.). Moreover, the withdrawal of aqueous humor can be at a site distinct from the delivery of the therapeutic agent, to reduce or eliminate the withdrawal of therapeutic agent that has previously been delivered.

In several embodiments, the device is configured to deliver the therapeutic agent at a rate between about 0.1 microliters per minute and about 100 microliters per minute. In several embodiments, the device is configured to deliver the therapeutic agent at a pressure between about 10 and about 40 mm of mercury.

In several embodiments, the device is configured to allow delivery of a therapeutic agent to a specific ocular target tissue, wherein the therapeutic agent comprises a plasmid. In several embodiments, the therapeutic agent comprises a polynucleotide encoding lysyl oxidase-like 1 (LOXL1), CYP1B1, myocilin, TGF-beta latency-associated peptide (LAP), prostaglandin F synthase, C3 transferase, caldesmon or variants thereof.

Also provided for herein, in several embodiments, is use of a device according the embodiments discussed herein, for the treatment of elevated intraocular pressure.

In several embodiments, there is provided a method of treating glaucoma, comprising assessing the intraocular pressure in the eye of a subject afflicted with glaucoma and exhibiting or being at risk for elevated intraocular pressure, introducing a delivery device into an anterior chamber of an eye of the subject, and delivering to the anterior chamber a therapeutic agent comprising a plasmid comprising a polynucleotide encoding a therapeutic gene based on the assessed intraocular pressure.

Depending on the embodiment, one or more of a volume, a concentration, a rate, a frequency, or a pressure of delivery of the therapeutic agent can optionally be selected based on the assessed intraocular pressure. In several embodiments, the therapeutic agent is delivered in a volume of about 10 to 1000 microliters. However, some embodiments further comprise removing a volume of fluid from the anterior chamber of the eye of the subject prior to delivering the therapeutic agent to the anterior chamber. Depending on the embodiment the removal and delivery is repeated between 2 and 10 times (e.g., about 5 to 8 times). In such embodiments, the repeated removal of fluid in the eye and replacement of the volume with a solution comprising the plasmid DNA, the amount of the plasmid DNA present in the anterior chamber increases. Thus, a maximized amount of plasmid DNA (and hence the therapeutic gene) can be delivered.

In several embodiments, the concentration of the therapeutic agent is between about 10 micrograms nucleic acid per milliliter to 5000 micrograms per milliliter. Rate of delivery of the therapeutic agent varies depending on the embodiment, but is generally between about 0.1 microliters per minute and about 100 microliters per minute. Delivery frequency may also vary (e.g., depending on the status and/or severity of the ocular disorder), but in several embodiments, the frequency of delivery is between once every four weeks and once every 2 years. Again, the state and/or severity of disorder may control, but in several embodiments, the therapeutic agent is delivered at a pressure between about 10 and about 40 mm of mercury. In several embodiments, the delivery (and/or withdrawal) is accompanied by a pressure measurement (optionally in real time) and the pressure of the anterior chamber is maintained within a desired pressure window.

Depending on the embodiment, the therapeutic agent may a polynucleotide encoding lysyl oxidase-like 1 (LOXL1), CYP1B1, myocilin, TGF-beta latency-associated peptide (LAP), prostaglandin F synthase, C3 transferase, caldesmon or variants thereof. Other genes that impact, directly or indirectly, intraocular pressure and/or fluid drainage may also be used. In several embodiments, the gene is controlled by an inducible or otherwise regulatable promoter.

In some embodiments, the therapeutic agent is delivered manually to the anterior chamber. In some embodiments, the therapeutic agent is delivered semi-automatically to the anterior chamber. In some embodiments, the therapeutic agent is delivered automatically to the anterior chamber.

In several embodiments, the methods further comprise generating and applying an electrical field focused across at least a portion of an intraocular tissue. In several embodiments, the intraocular tissue is the trabecular meshwork. In some embodiments, the intraocular tissue is the ciliary body. In several embodiments, the application of the focused electrical field is achieved by the use of an electroporation apparatus, which may comprise at least one positive and at least one negative electrode. In some embodiments, the electroporation apparatus comprises a plurality of positive electrodes and a plurality of negative electrodes. In some embodiments, the plurality of positive electrodes are positioned in an arcuate housing shaped to mimic a curvature of the outside of the eye of the subject, and wherein the plurality of negative electrodes are positioned in an arcuate housing shaped to mimic a curvature of the outside of the opposite side (or another portion that is not opposite) of the eye of the subject. Optionally, the plurality of positive and negative electrodes are equal in number. In some embodiments, employ a control module that controls an activation of a percentage of the plurality of positive electrodes and of the plurality of negative electrodes. In an embodiment, the intraocular tissue is the trabecular meshwork and the electrical field is applied at a voltage between 100 mV and 100 V, using between 1 and 20 pulses, wherein the pulses are applied for a duration of between 0.5 and 10 milliseconds per pulse, and wherein the pulses are separated by an interval of between about 20 to 150 milliseconds.

Also provided herein are devices for generating and applying an electrical field to an ocular target tissue, comprising a first arcuate housing in which is positioned a plurality of positive electrodes, a second arcuate housing in which is positioned an plurality of negative electrodes, wherein the first and second arcuate housings are adjustable with respect to one another to yield an ovoid shape of a desired dimension, the desired dimension corresponding to the shape of an outer surface of an eye of a subject.

In several embodiments the device is configured to apply an electrical field focused on the trabecular meshwork of the eye of the subject. Other ocular tissues may also be targeted, for example the ciliary body.

In one embodiment, the plurality of positive and plurality of negative electrodes are equal in number.

In several embodiments, the device also includes a control module configured to accept user input related to a percentage of the plurality of positive and negative electrodes to be activated during the application of the electrical field to a specific ocular target tissue. In several embodiments the device also includes an injection system that comprises a first syringe configured to perfuse a therapeutic agent and a second syringe configured to withdraw aqueous humor. In several embodiments, the device also includes a pressure transducer configured to detect an intraocular pressure of the eye.

Also provided are embodiments of an injection system, comprising a plurality of syringes, a needle configured to deliver plasmid DNA, a tubing to connect the needle and the plurality of syringes, and a plurality of plungers. In several embodiments, the plurality of syringes of further comprises a stopcock residing within each of the plurality of syringes. In several embodiments, each stopcock further comprises a button.

In one embodiment, the plurality of plungers comprises a first plunger and a second plunger, the first plunger coupled to a first syringe of the plurality of syringes and the second plunger coupled to a second syringe of the plurality of syringes.

Depending on the embodiment the plurality of plungers and/or stopcocks are manually operated, semi-automatically operated, or automatically operated.

In several embodiments, the plurality of syringes comprises a first syringe configured to deliver a fluid to a target space and a second syringe configured to withdraw fluid from a target space. In one such embodiment, the delivery syringe is configured to deliver up to about 250 microliters of fluid at a time. In an additional embodiment the withdrawal syringe is configured to withdraw up to about 250 microliters of fluid at a time. In several embodiments, the system is configured to alternately withdraw a fluid and deliver plasmid DNA repeatedly.

Some embodiments also include a transducer housing comprising a display coupled to an outer surface of the transducer housing, a pressure transducer, and a diaphragm. In several embodiments, the pressure transducer housing is removable. Optionally, the pressure transducer housing further comprises a jack, which can be configured to connect to a controller, to connect to a pump, to connect to an amplifier, or to connect to any combination of these (analog or digital).

Also provided herein are kits for the delivery of plasmid DNA to a target tissue, comprising a plasmid comprising a gene of interest, a buffer that is biocompatible and configured to solubilize the plasmid, thereby making the plasmid suitable for delivery by injection, an injection device, and instructions for use. In several embodiments, the plasmid comprises a therapeutic gene, which can optionally be selected from lysyl oxidase-like 1 (LOXL1), CYP1B1, myocilin, TGF-beta latency-associated peptide (LAP), prostaglandin F synthase, C3 transferase, caldesmon or variants, truncations, mutants, or fragments thereof. In several embodiments, the therapeutic gene comprises a gene that directly or indirectly promotes therapeutic changes to intraocular pressure. In several embodiments, the plasmid further comprises a reporter element. In additional embodiments the plasmid further comprises an inducible element. In some embodiments, the injection device comprises an injection syringe, a withdrawal syringe, a tubing in fluid communication with the injection syringe and the withdrawal syringe, a needle in fluidic communication with the tubing, and a pressure transducer in fluidic communication with the tubing. In some embodiments, the kit further comprises an electroporation apparatus configured to apply an electric field to the target tissue. Optionally, the kit may also further comprise a plurality of additional plasmid DNA, wherein the additional plasmid DNA, optionally comprise a different therapeutic gene, optionally comprise a different amount of plasmid DNA, optionally comprise a different orientation of the same therapeutic gene, optionally comprise different inducible elements, or optionally comprise a different promoter.

Also provided herein is use of a plasmid DNA comprising a therapeutic gene to treat or prevent elevated intraocular pressure, wherein the plasmid DNA is configured for delivery to an anterior chamber of an eye of a subject having or prone to elevated intraocular pressure, the delivery of the plasmid DNA configured to induce expression of the therapeutic gene in tissues of the eye such as trabecular meshwork and ciliary body. Devices and systems for this use are also described herein, and any combination of the features of the devices and/or systems can be applied in a specific use of a plasmid DNA comprising a therapeutic gene to treat or prevent elevated intraocular pressure.

BRIEF DESCRIPTION OF THE DRAWINGS

The foregoing and other features, aspects and advantages of the embodiments of the invention are described in detail below with reference to the drawings of various embodiments, which are intended to illustrate and not to limit the inventions disclosed herein. The drawings comprise the following figures, in which:

FIG. 8 is a schematic depicting an embodiment of an injection system.

FIG. 9A is a schematic depicting a top view of an embodiment of an injection system.

FIG. 9B is a schematic depicting a bottom view of an embodiment of an injection system.

DETAILED DESCRIPTION

Figure 1:
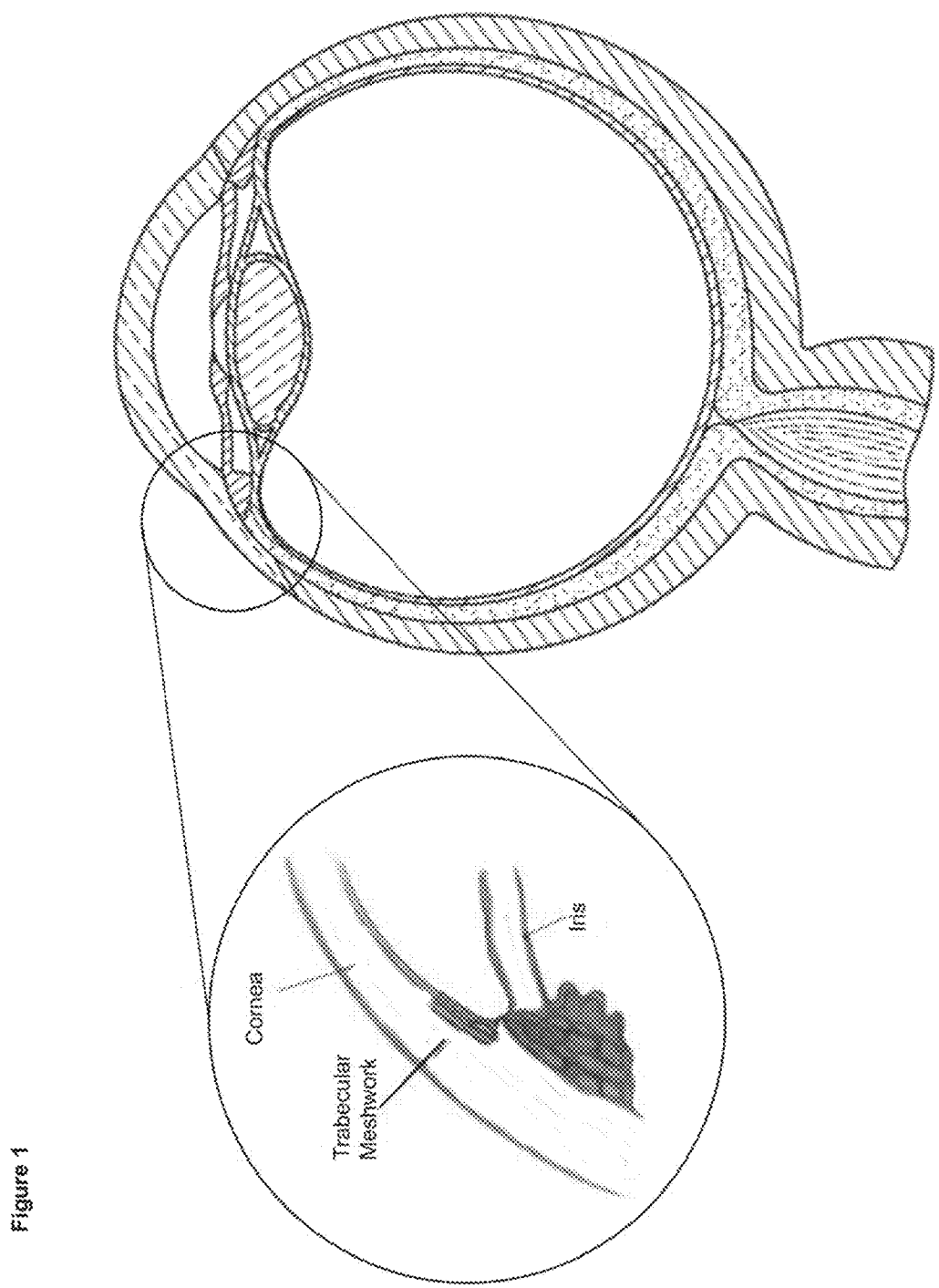
FIG. 1 depicts a cross-sectional side view of an eye.
Figures 2A, 2B:
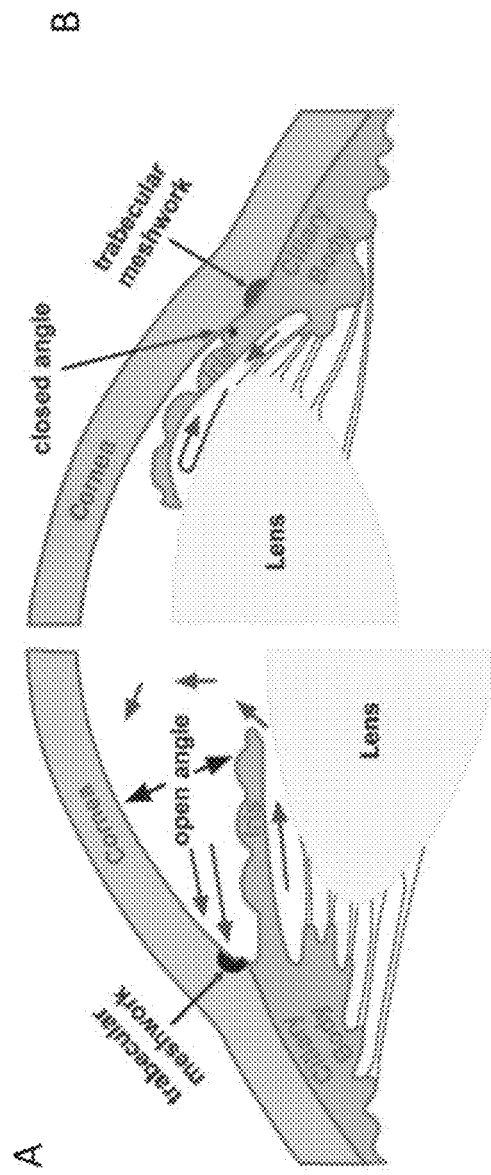
FIGS. 2A-2B show a schematic of an eye, contrasting flow with an open angle (2A) and a closed angle between the iris and cornea (2B).

Although several embodiments, examples and illustrations are disclosed below, it will be understood by those of ordinary skill in the art that the invention described herein extends beyond the specifically disclosed embodiments, examples and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

The disclosure herein provides methods, systems, and devices for treatment of ocular disorders through the delivery of therapeutic nucleic acids that dramatically improve the ability to efficiently control treatment of those disorders. In traditional systems for treating ocular disorders, drugs and/or medication may be provided to an anterior chamber of the eye, but the dosage of drugs and/or medication cannot be effectively controlled. Additionally, the titration of ocular fluid outflow is typically imperfect. The disclosure herein provides embodiments that effectively prevent or control elevated intraocular pressure. In some embodiments, the methods, systems, and devices for treatment of ocular disorders may apply a pressure and/or a volume throughout treatment.

In traditional systems for treating ocular disorders, doctors may not be able to efficiently control the target location of introduced plasmids, drugs, and/or other medication. The disclosure herein provides embodiments that leverage the flow of introduced plasmids, drugs, and/or other medications across the anterior chamber of the eye and to a physiological outflow space, such as the trabecular meshwork. Traditional systems for treating ocular disorders may result in several complications and risks, such as eye pressure that is too high or too low, inflammation, discomfort, and/or scarring. Provided herein are embodiments that reduce the risk of complications by effectively controlling the delivery, amount and targeting of a therapeutic agent.

In traditional systems for treating ocular disorders, such as surgery, many complications may arise including bleb leaks, infections, scarring, cataracts and/or other side effects. Additionally, after other types of traditional surgery, patients could require daily eye drops or other topical medications. Traditional types of drug administration would require significant patient compliance to completely treat the particular ocular disorder. Pressure control in the eye may also be lost after traditional methods of surgery.

The disclosure herein provides embodiments that may reduce those complications, among others. Embodiments disclosed herein effectively and efficiently monitor pressure in the eye, accurately determine the pressure and volume of delivery of compositions comprising DNA plasmids necessary for treatment, properly place an injection apparatus in or near the eye, and/or control the systems and processes throughout the entire treatment. In some embodiments, the treatment systems may be manual, semi-automatic, and/or automatic. Several embodiments disclosed herein also require reduced patient involvement with respect to compliance in treating ocular disorders. In some embodiments, electroporation may be used to direct DNA plasmids in the anterior chamber of the eye once the plasmids have been injected. Electroporation may also enhance gene delivery to the trabecular meshwork or ciliary body in the eye. In several embodiments, this aids in the reduction of scarring, inflammation, and/or other side effects.

Several traditional systems for treating ocular disorders, such as drainage implants, may result in very low eye pressure, cataracts, breakdown of the cornea detached choroid and/or retina, and/or eye movement disorders. Often, additional surgery may become necessary as implants fail or become blocked. The disclosure herein provides for systems, devices and methods that effectively and efficiently monitor eye pressure and determine the appropriate amount of DNA plasmids necessary for treatment. Thus, through several embodiments, complications associated with traditional systems of treating ocular disorders may be substantially reduced.

To achieve the foregoing improvements in the technical field of medical treatment systems, the systems disclosed herein employ a variety of features, techniques, and methodologies. The new features, techniques and methodologies disclosed herein solve problems that specifically arise in the realm of ocular disorders, specifically in treating glaucoma. Even though the systems disclosed herein are primarily described to treat glaucoma, the disclosed systems can be used to treat other disorders related to the eye or any bodily organ.

Ocular Anatomy

The eye is a specialized sensory organ that detects light and converts it into electrochemical impulses in neurons, thereby allowing for vision. The eye has multiple chambers, namely the anterior chamber (filled with aqueous humor of about 250 microliters in humans), the posterior chamber (a small space posterior to the iris, but anterior to the lens), and the vitreous chamber (the most posterior of the three chambers). The anterior chamber lies between the outer surface of the eye, the cornea and the iris. Aqueous humor is secreted from the ciliary body and flows into the anterior chamber. Aqueous humor has multiple functions, including, but not limited to, maintaining the intraocular pressure and inflating the globe of the eye, providing nutrition to the cornea the trabecular meshwork the lens and other anterior chamber anatomical structures, and providing refractive index for enhanced visual acuity. Aqueous humor is produced continually and therefore maintenance of intraocular pressure must be balanced by an equal rate of aqueous humor drainage.

Aqueous humor drains from the anterior chamber through the trabecular meshwork into Schlemm's canal. Schlemm's canal allows flow of aqueous humor to the episcleral veins. As the primary regulator of outflow, the trabecular meshwork provides the greatest resistance to aqueous flow. The trabecular meshwork handles up to 90% of aqueous outflow. The tissue is highly elastic and contractile, and thus regulates fluid flow and therefore plays an important role in regulating IOP. A pathological change in mechanisms regulating trabecular meshwork elasticity and contractility could adversely affect aqueous outflow and IOP and cause glaucoma. A secondary route of outflow is via uveoscleral drainage (which is independent of the intraocular pressure), but this route normally accounts for much less drainage than the trabecular meshwork.

Ocular Disorders

As discussed above, the balance of production and drainage of aqueous humor is required for maintenance of normal intraocular pressure. Glaucoma is a progressive disease that destroys retinal ganglion cells and their axons causing a corresponding loss of vision. It is the leading cause of irreversible blindness worldwide, and, to date, is incurable. Elevated intraocular pressure, either through increased production or decreased outflow of aqueous humor, is associated with glaucoma. The elevation in intraocular pressure can be caused, for example, by abnormal trabecular meshwork or to damage of the meshwork due to injury or disease of the iris.

Various types of glaucoma exist, with a primary categorization being whether the glaucoma is open-angle or closed angle glaucoma. The angle in question refers to the angle between the iris and the cornea. When this angle is narrowed or closed, pressure can build up, and eventually damage the optic nerve leading to loss of vision.

Primary open-angle glaucoma is a result of progressive clogging of the drainage canals resulting in increased eye pressure which causes progressive optic nerve damage. This is the most common type of glaucoma, accounting for 90% of cases in the United States. Onset is slow and painless, and loss of vision is gradual and irreversible. In narrow and closed angle glaucoma the iris bows forward, narrowing the angle that drains the eye, increasing pressure within the eye. If untreated, it can lead to the medical emergency of angle closure glaucoma. In angle closure glaucoma (closed angle glaucoma) the iris bows forward and leads to physical contact between the iris and trabecular meshwork, thereby blocking outflow of the aqueous humor from within the eye. This contact can lead to increasing compromise to the function of the trabecular meshwork until it fails to keep pace with aqueous production, and the intraocular pressure rises. Onset of symptoms is sudden, and causes pain and other symptoms that are noticeable, and is treated as a medical emergency.

Secondary glaucoma refers to cases in which another disease, trauma, drug or procedure causes increased eye pressure, resulting in optic nerve damage and vision loss.

In exfoliation glaucoma, the pressure is due to the accumulation of microscopic granular protein fibers, which can block normal drainage of the aqueous humor. In essence, debris clogs the outflow passage of the trabecular meshwork. Similarly, pigmentary glaucoma results from sloughing off of pigment cells from the back of the iris, which then collect in the anterior chamber and can clog the trabecular meshwork. Polymorphisms of the lysyl oxidase-like 1 (LOXL1) gene are associated with exfoliation syndrome, in which elevated intraocular pressure and glaucoma develops. The glaucoma that develops in exfoliation syndrome is particularly aggressive. LOXL1 is involved in maintaining elastic fibers, and LOXL1 deficiency leads to elastic derangements in tissues. In the trabecular meshwork, intraocular pressure dysregulation and elevation are thought to result because of this.

An animal model in which exfoliation syndrome may be explored is the LOXL1 homozygous knockout (LOXL1−/−) mouse, which is discussed in more detail below. LOXL1−/− mice are born with normal elastin content, but this content diminishes with age due to impaired elastin maintenance over time. As discussed below, the ability to correct the trabecular meshwork LOXL1 abnormality early in the course of the exfoliation syndrome could allow the prevention of elevated intraocular pressure and glaucoma related to LOXL1 anomalies.

Primary juvenile glaucoma is a neonate or juvenile abnormality where ocular hypertension is evident at birth or shortly thereafter and is typically a result of anatomical abnormalities in the anterior chamber angle development that can result in the blockage of aqueous humor outflow.

Uveitic glaucoma is a result of uveitis (swelling and inflammation of the uvea, the middle layer of the eye). Increased eye pressure in uveitis can result from the inflammation itself or from the steroids used to treat it.

As is discussed in more detail below, effectively managing, treating, and eventually curing or relieving glaucoma long term can result, in several embodiments, from correction of the molecular defects in tissues responsible for intraocular pressure abnormality (such as, for example, the trabecular meshwork).

Glaucoma Treatments

As discussed above, glaucoma can result from the overproduction of aqueous humor and/or more commonly impaired drainage of aqueous humor. Glaucoma therapies have therefore typically focused on one or both aspects of aqueous humor production or drainage. One therapeutic approach involves drug treatment to reduce the production of aqueous humor by the ciliary body. However, drug dosage over time must be regularly monitored and at times patient compliance can result in less than desired therapeutic effects. Additionally, drug therapies can often impart side effects that require additional medications to counteract the side effects, which can further reduce patient compliance. Another approach focuses more specifically on enhancing or augmenting the outflow of aqueous humor by, for example, stenting the trabecular meshwork (or even by passing the meshwork in its entirety). One drawback these approaches are the invasiveness of the procedures. Additionally, because these are physical approaches, they may also be subject to the same progressive degradation of outflow efficacy over time as the trabecular meshwork itself was. For example, a stent may provide enhanced outflow shortly after implantation, but may slowly become occluded over time, thereby necessitating an additional invasive surgery to clear and/or replace the stent. Some approaches couple drug delivery with a physical stent, while still additional approaches using implantable device to deliver a drug more precisely to a target tissue to enhance drainage of aqueous humor. While these approaches may have certain drawbacks, several embodiments of the methods disclosed herein are configured to dovetail with these approaches to provide an enhanced therapeutic effect in the treatment of glaucoma.

Molecular approaches have also been used in an attempt to treat glaucoma primarily, for example, gene therapy. However, as will be discussed in more detail below, gene therapy typically employs a viral vector for delivery of a therapeutic gene of interest which, when used in the intraocular environment present several limitations and potential drawbacks, such as immunogenic risks. While certain viral vectors (such as adeno-associated viruses (AAV)) have been applied to retinal gene therapy with some success, these vectors present issues with gene carrying capacity, and they still retain some capacity to incite immune responses and malignancy.

Plasmids as Vectors

In contrast to viral vectors, nonviral naked DNA, such as plasmid DNA, has a significantly reduced or nonexistent immunogenic and/or safety risk. Further advantages are realized when using plasmid DNA, such as the fact that there is little size limitation of the therapeutic gene of interest that can be incorporated into a plasmid DNA vector. Thus a wide variety of therapeutic genes can be evaluated for a given disease, whereas the pool of therapeutic genes that are sufficiently small to fit within a viral vector may be much reduced. Additionally, plasmid DNA is very stable, does not necessarily require refrigeration or freezing to maintain the stability long-term, and has a long history of use in a laboratory environment. Taken together, many of the characteristics of plasmid DNA generically are understood, which makes plasmid DNA an ideal choice for several of the therapeutic embodiments disclosed herein. Still further, plasmids allow a certain degree of flexibility on the orientation in which a gene is inserted into the plasmid (genes may be inserted with the N-terminal region or the C-terminal region of a polypeptide encoding a therapeutic gene of interest in a desired position within the plasmid). This ability to change the orientation of the therapeutic gene of interest provide certain advantages that will be appreciated by one of ordinary skill in the art. Additionally, as discussed above, plasmids have few, if any, size restrictions and therefore even with large therapeutic genes, there remains the capacity for integrating a marker or other type of reporter gene into the plasmid (such as for example green fluorescent protein, red fluorescent protein, or some other identifiable marker that could be used as a quality control for delivery and determination of the long-term lifespan of the therapeutic gene within a target cell).

Therapeutic Genes

As discussed above, a variety of types of ocular disorders exist that are related to or otherwise associated with increased intraocular pressure. Thus, in accordance with several embodiments disclosed herein any therapeutic gene that can be used to reduce intraocular pressure to a normal level or prevent pressure elevation can be used with the methods, devices, and systems disclosed herein. Depending on the embodiment, a therapeutic gene can be used to reduce symptoms of and/or treat disorders associated with increased intraocular pressure by one of three main conceptual pathways, namely, reducing the production of intraocular fluid; increasing the outflow of intraocular fluid; and preventing disease-related decline of outflow.

For example, in one embodiment a polynucleotide encoding lysyl oxidase-like 1 (LOXL1) can be administered in the treatment of exfoliation glaucoma. One example of such a nucleotide is NCBI Reference Sequence: NM_005576.2. In one embodiment a polynucleotide encoding myocilin can be used in the treatment of juvenile glaucoma. In one embodiment, a polynucleotide encoding CYP1B1 can be used in the treatment of childhood and/or adult glaucoma. In one embodiment, a polynucleotide encoding prostaglandin F synthase can be administered in order to induce ocular tissues to up regulate production of prostaglandins, which can be used to supplement (or even replace) use of a daily prostaglandin eye drop. In still additional embodiments, a polynucleotide encoding C3 transferase or caldesmon can be administered in order to reduce the contractility of intraocular and/or extraocular muscles (for example by inhibition of ATPase activity of myosin), which, as a secondary effect can reduce pressure on the eye as a whole.

Depending on the embodiment, fragments, derivatives, mutants, truncations, or other variants of a therapeutic gene of interest can be used. These terms shall be given their ordinary meanings. They may also refer to a polynucleotide that is at least 40%, 45%, 50%, 55%, 60%, 65%, 70%, 75%, 80%, 85%, 90%, 95%, 98% or 99% identical to a native (e.g., wild type) polynucleotide; a polynucleotide that encodes a polypeptide that is least 40%, 45%, 50%, 55%, 60%, 65%, 70%, 75%, 80%, 85%, 90%, 95%, 98% or 99% identical to a native polypeptide; a polynucleotide that encodes a polypeptide that contains 1, 2, 3, 4, 5, 6, 7, 8, 9, 10, 11, 12, 13, 14, 15, 16, 17, 18, 19, 20 or more amino acid mutations (e.g., additions, deletions and/or substitutions) relative to a native polypeptide; a polynucleotide that encodes a polypeptide that can hybridize under high, moderate or typical stringency hybridization conditions to nucleic acids encoding a native polypeptide; or a polynucleotide that encodes a polypeptide that can hybridize under high, moderate or typical stringency hybridization conditions to a nucleic acid sequence encoding a fragment of a native polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids.

Additionally, derivatives, fragments, or variants of native polynucleotides include those that encode polypeptides that retain at least 20%, at least 30%, at least 40%, at least 50%, at least 60%, at least 70%, at least 80%, at least 90%, at least 95%, at least 96%, at least 97%, at least 98%, at least 99% of the activity of a native polypeptide.

As discussed above, the therapeutic gene may optionally integrate or be placed in line with a reporter gene. Suitable reporter gene include, but are not limited to, lacZ, chloramphenicol acetytransferase, green fluorescent protein, red fluorescent protein, or any other reporter disclosed herein or that is suitable for use in human therapy.

In some embodiments, the plasmid DNA also includes an inducible element that either positively or negatively regulates gene expression of the therapeutic gene. Depending on the embodiments, either chemically regulated or physically regulated inducible elements are used. Physically regulated inducible elements include, but are not limited to those that react to light (e.g., light intensity), temperature, such as a physiological temperature as would be found in an intraocular environment, etc. Chemically regulated inducible elements include, but are not limited to, those that respond to regulate gene expression based on the presence or absence of, for example, alcohol, a drug such as tetracycline, doxycycline, etc., steroid compounds, metal or metal ions, etc. Some embodiments utilize, for example a Cre-lox inducible system. Some embodiments employ for example, a Tet-on/Tet-off system (or other drug-based regulation system. Some embodiments employ a myxovirus resistance 1 (Mx1) promoter, which is inducible by interferon α and γ as well as the dsRNA analog poly(I:C). As mentioned above, positive and/or negative regulation of the therapeutic gene can be achieved using such a system. Other mechanisms can also be used to regulate expression of the therapeutic gene, such as for example short interfering RNA, shRNA, etc. In some embodiments the regulator of gene expression is advantageously light sensitive. In some embodiments, the regulator is administered topically or orally.

In addition to other advantages, delivery of plasmid DNA including a therapeutic gene of interest can also include use of a tailored promoter driving the expression of the therapeutic gene, in some embodiments, tissue specific promoters are used in order to reduce or avoid off target effects. In particular embodiments, however, promoters that are not tissue specific are used. In some embodiments well-established high-efficiency promoters are used such as for example cytomegalovirus (CMV) promoters.

Delivery and Adjunct Devices

As discussed more fully below, devices and systems to deliver naked plasmid DNA can vary depending on the embodiment. For example in some embodiments a delivery device comprises an injection syringe that delivers the desired volume of plasmid DNA to the target tissue (e.g., ocular tissue) of a subject. In some embodiments, the delivery device incorporates and/or communicates with a manometer, in order to deliver the plasmid DNA to the ocular tissue of the subject within the desired pressure window. Some embodiments comprise a computer interface that allows dynamic adjustment of one or more delivery variables (e.g., pressure, volume, rate, duration of infusion etc.). In some such embodiments, adjunct methods, such as application of an electric field to the ocular tissue, can also be controlled by a computer interface.

Figure 3:
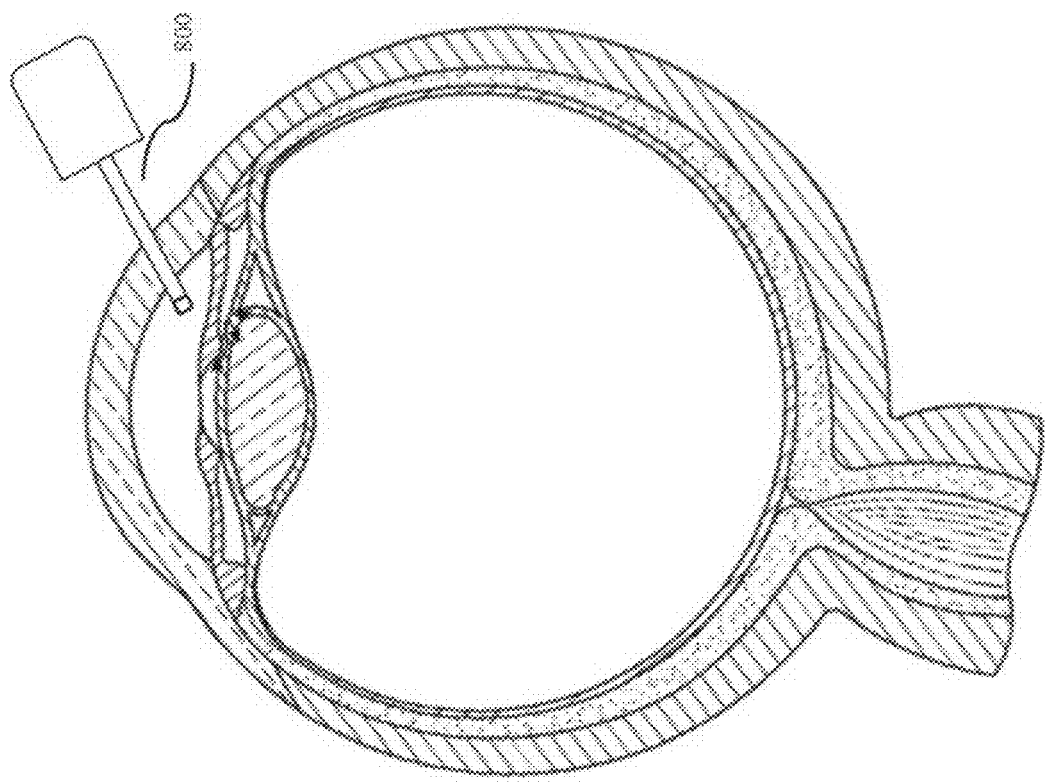
FIG. 3 depicts a cross-sectional side view of an eye comprising an embodiment of an injection system.

FIG. 3 illustrates an embodiment of an injection system 800. In an embodiment, a needle 802 of the injection system 800 may touch an anterior chamber of the eye. In an embodiment, the injection system 800 delivers plasmid DNA to the ocular tissue.

Figure 4:
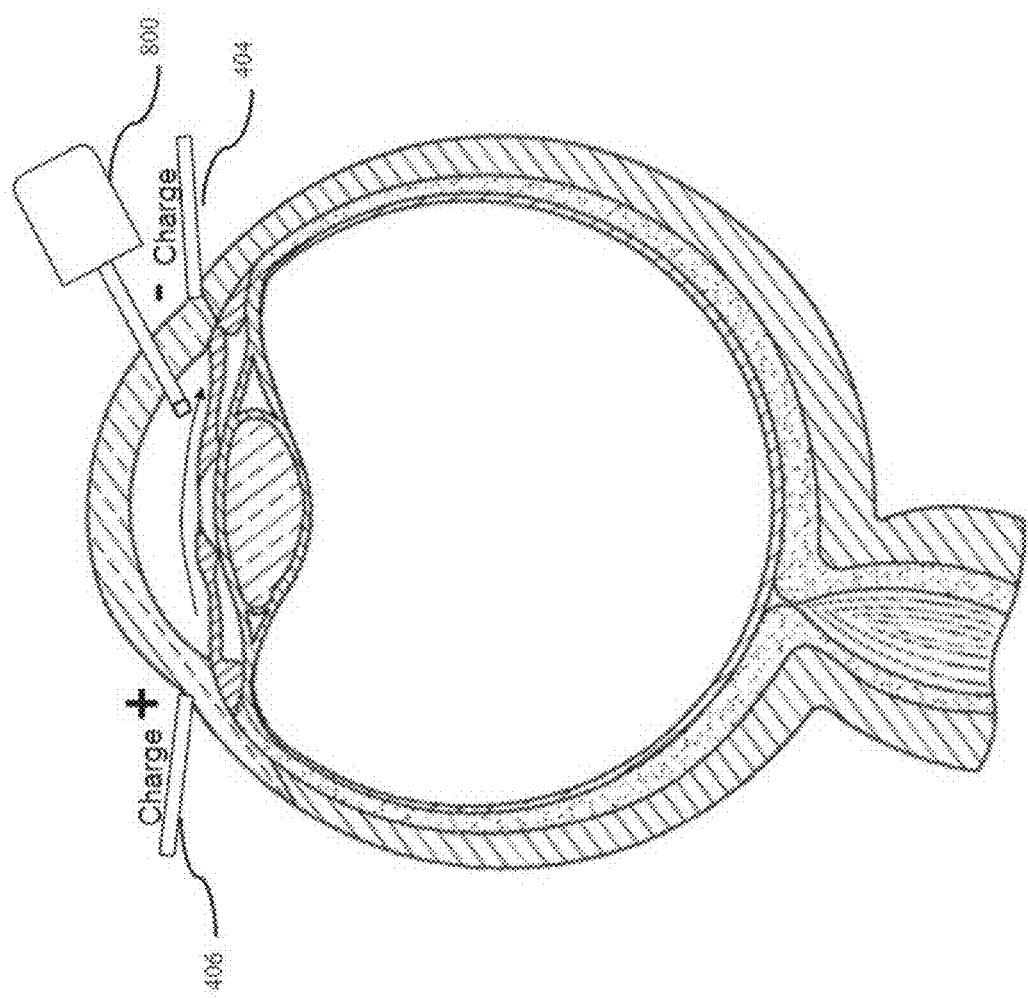
FIG. 4 depicts a cross-sectional side view of an eye comprising an embodiment of an injection system and electrically charged probes.

FIG. 4 illustrates another embodiment, in which the needle 802 of the injection system 800 may touch, pierce, penetrate, or otherwise enter the anterior chamber of the eye. In an embodiment, a negatively charged electrode 404 may be disposed on one side of the eye. In an embodiment, a positively charged electrode 406 may be disposed on another side of the eye. In an embodiment, one, two, three, four, or five or more electrodes may have a positive or a negative charge. In an embodiment, the one, two, three, four, or five or more electrodes may be disposed on opposing sides of the eye. Each of the one, two, three, four or five or more electrodes disposed on opposing or different sides of the eye may have opposite charges. Disposing oppositely charged electrodes on opposite sides of the eye may advantageously enhance the ability to control the flow direction of injected DNA plasmids from one side of eye to the other. It shall be appreciated that, depending on the embodiment, there need not be a balance of charges across the eye (e.g., one portion of the eye can be contacted with 3 electrodes while an opposite portion is contacted with only 1 electrode). Likewise, the positioning of the electrodes need not be truly opposite (e.g., angles of less than 180 degrees between electrodes may be used).

Figure 5:
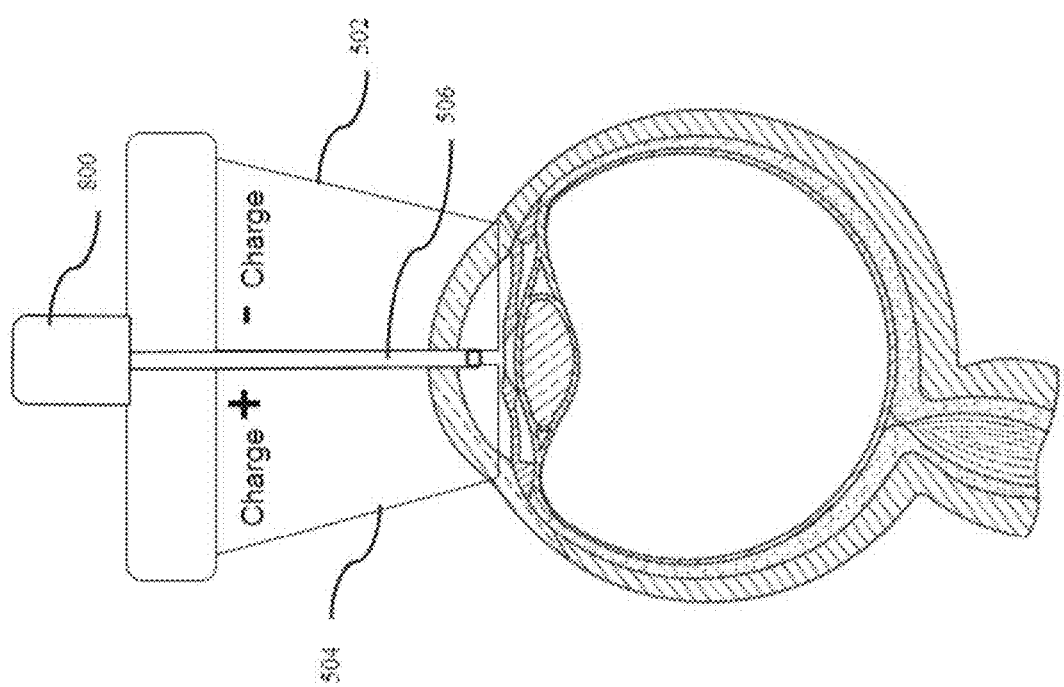
FIG. 5 depicts a cross-sectional side view of an eye comprising an embodiment of an electroporation system.

FIG. 5 illustrates an embodiment of an electroporation system. In an embodiment, a negatively charged electroporation plate 502 may be coupled to a positively charged electroporation plate 504. Side walls of the negatively charged electroporation plate 502 and the positively charged electroporation plate 504 may be sloped downwards. This would allow the electroporation system to fit over the anterior chamber of the eye. In some embodiments, the electroporation system may be adjustable to adapt to various sizes of the eye. In an embodiment, the injection system 800 is coupled to the electroporation system. In other embodiments, the injection system 800 can be placed in the center of the electroporation system. In an embodiment, a syringe 506 of the injection system 800 can be rotated about the center or to the side of the electroporation system. This allows the DNA plasmids to be injected at various angles and avoid trauma and scarring of certain eye structures. Disposing oppositely charged electroporation plates on opposite sides of the eye may advantageously enhance the ability to control the flow direction of injected DNA plasmids from one side of eye to the other.

Figures 6A, 6B:
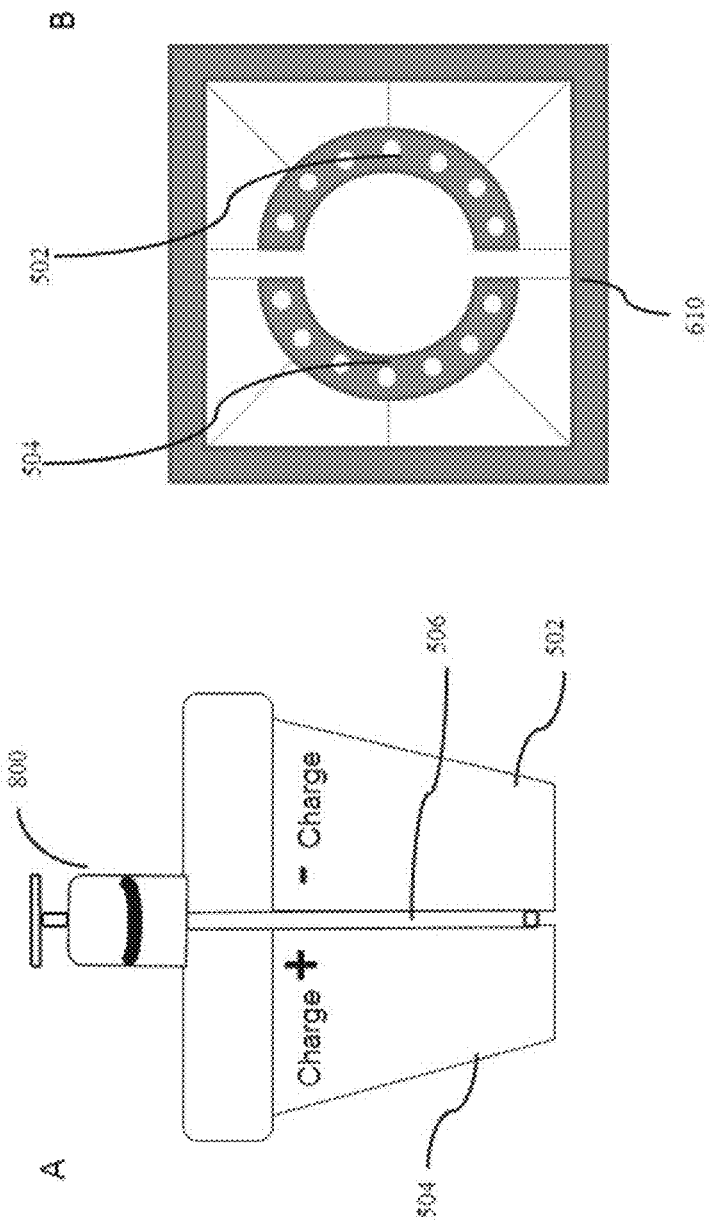
FIG. 6A is a schematic of a side view of an embodiment of an electroporation system.
FIG. 6B is a schematic of a top view of an embodiment of an electroporation system.

FIG. 6A illustrates an embodiment of the electroporation system. An embodiment of the electroporation system may comprise the positively charged electroporation plate 502, the negatively charged electroporation plate 504 and/or the syringe 506 of the injection system 800. FIG. 6B illustrates a top view of an embodiment of the electroporation system. In an embodiment, the positively charged electroporation plate 502 and the negatively charged electroporation plate 504 may have a semi-circular shape, rectangular shape, circular shape and/or any other shape, In an embodiment, an electroporation housing 610 may be rectangular, semi-circular, circular and/or any other shape.

Figures 7A, 7B, 7C:
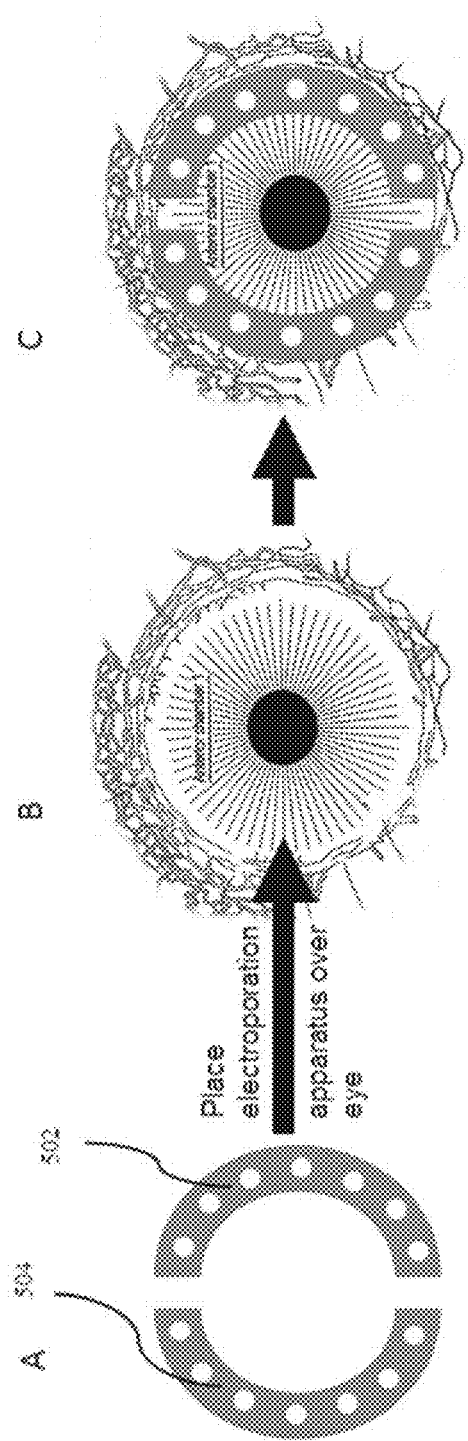
FIGS. 7A-7C is a flow chart depicting a method for placing an embodiment of an electroporation system over an anterior chamber of an eye.
Figure 10:
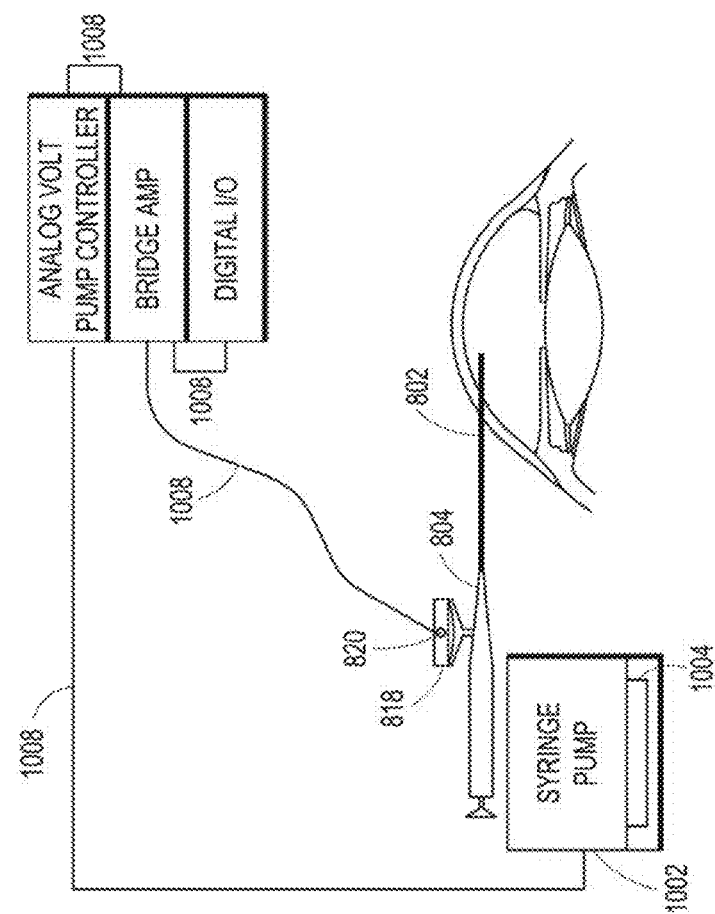
FIG. 10 is a schematic of an embodiment of the connections between an injection system and a pump.

FIGS. 7A-7C illustrate a schematic top view of an embodiment of a process for placing the electroporation system over the eye. As illustrated, the electroporation system is placed over the anterior chamber of the eye.

FIG. 8 is a schematic of an embodiment of the injection system 800. In an embodiment, the injection system 800 may comprise one, two, three, four, five, or six or more syringes or other injection devices. In an embodiment, the injection system 800 can be manually operated, semi-automatic, and/or fully-automatic. In an embodiment, the injection system 800 can be configured to withdraw and/or perfuse.

In an embodiment, the injection system 800 may comprise the needle 802, a Y-tubing 804, a perfusion syringe 806, a withdrawal syringe 808, a stopcock 810, a display 812, a first plunger 814, a second plunger 816, and/or a pressure transducer housing 818. The needle 802 may be coupled to a first portion 822 and/or a second portion 824 and/or a third portion 826 of the Y-tubing 804. In some embodiments, the Y-tubing 804 may be non-distensible.

The injection system 800 may comprise a pressure transducer which may reside in the pressure transducer housing 818. In an embodiment, a diaphragm 902 and/or a Wheatstone bridge may also reside in pressure transducer housing 808. In an embodiment, the pressure transducer housing 818 may be detachable from the injection system 800.

In some embodiments, the pressure transducer housing 818 may be coupled to the second portion 824 of the Y-tubing 804. In other embodiments, the pressure transducer housing 818 may be coupled to a junction formed between the first portion 822, second portion 824, and/or third portion 826 of the Y-tubing 804 or any other portion of the Y-tubing 804 and/or any portion of the injection system 800. Still, in other embodiments, the pressure transducer housing 818 may be coupled to the perfusion syringe 806 and/or the withdrawal syringe 808. In an embodiment, the pressure transducer housing 818 may be coupled to the needle 802. In other embodiments, the pressure transducer housing 818 may be coupled to the first plunger 814 and/or the second plunger 816.

The display 812 can be coupled to an outer surface of the pressure transducer housing 818. The display 812 can be analog and/or digital and may comprise a dial in some embodiments. The display 812 may be configured to display a pressure determined by the pressure transducer. In an embodiment, a jack 820 may be coupled to a second outer surface of the pressure transducer housing 818. The jack 820 may be configured to connect to a controller and/or a pump 1002. The controller may be analog or digital in some embodiments.

In an embodiment, perfusion syringe 806 may be comprised of the first plunger 814. In this embodiment, the perfusion syringe 806 can be configured to inject a maximum of 250 microliters. In other embodiments, perfusion syringe 806 may be configured to inject more than 250 microliters. In some embodiments, the perfusion syringe 806 may be pre-filled with medication, DNA, plasmids, and/or any other substance. In other embodiments, the perfusion syringe 806 may not be pre-filled. Perfusion syringe 806 may be made of glass.

In an embodiment, withdrawal syringe 808 may comprise the second plunger and a stopcock 810. Stopcock 810 may comprise a button for opening and/or closing the withdrawal syringe 808. In some embodiments, withdrawal syringe 808 can be preset to zero microliters and can be configured to withdraw a maximum of 125 microliters. In other embodiments, withdrawal syringe 808 can be configured to withdraw more than 125 microliters.

FIGS. 9A-9B are schematic diagrams depicting an embodiment of the injection system 800. FIG. 9A is side view of an embodiment of the perfusion syringe 806. FIG. 9B is a side view of an embodiment of the withdrawal syringe 808. In an embodiment, the pressure transducer housing 818 is coupled to the perfusion syringe 806 by a lumen linking chamber 904. In an embodiment, the diaphragm 902 of the pressure transducer housing 818 is coupled to a button 908 of a first stopcock 906. In an embodiment, the diaphragm 902 can be piezoelectric. Based on the specified pressure indicated by the pressure transducer residing within the pressure transducer housing 818, the first stopcock 906 can be configured to open and close to allow the proper amount of medication and/or DNA to be injected.

The injection system 800 can be used in several ways. In one example, injection system 800 can be configured to exchange 50% aqueous liquid with a medication and/or DNA to a transduced pressure. In an embodiment of this process, perfusion syringe 806 can be set to its maximum injection capacity of 250 microliters. The needle 802 can be inserted into an anterior chamber of the cornea. Next, a second stopcock 910 can be opened. Next, the second plunger 816 of withdrawal syringe 808 can be pulled back to withdraw a maximum of 125 microliters aqueous liquid. After, the first stopcock 906 can be opened and the medication and/or DNA residing in perfusion syringe 806 can be injected by pushing the first plunger 814 to replace the withdrawn aqueous liquid. Once the withdrawn aqueous liquid is replaced, the first plunger 814 can be pressed further to inject the medication and/or DNA to increase the transduced pressure. Once the pressure reaches the level of the transduced pressure, the needle 802 can be withdrawn to complete the process.

In another embodiment, the pump 1002 can be connected to the jack 820 by a connector 1008. In an embodiment, connector 1008 may connect the jack 820 to a bridge amp, and/or the bridge amp to a digital input and/or output, and/or the bridge amp to an analog volt pump controller, and/or the analog volt pump controller to the pump 1002. This is advantageous for longer perfusions because this embodiment allows for the transduced pressure (e.g., 35 mmHg, 15 mmHg, 25 mmHg and/or 15 mmHg to 35 mmHg) to be fixed and/or controlled over the period of the perfusion. The transduced pressure may be determined by inserting the needle 802 into the anterior chamber of the cornea. In an embodiment, the pump 1002 of the perfusion syringe 806 may comprise an inbuilt analog voltage integrator 1004. In an embodiment, the pump 1002 may comprise a display.

Figure 12:
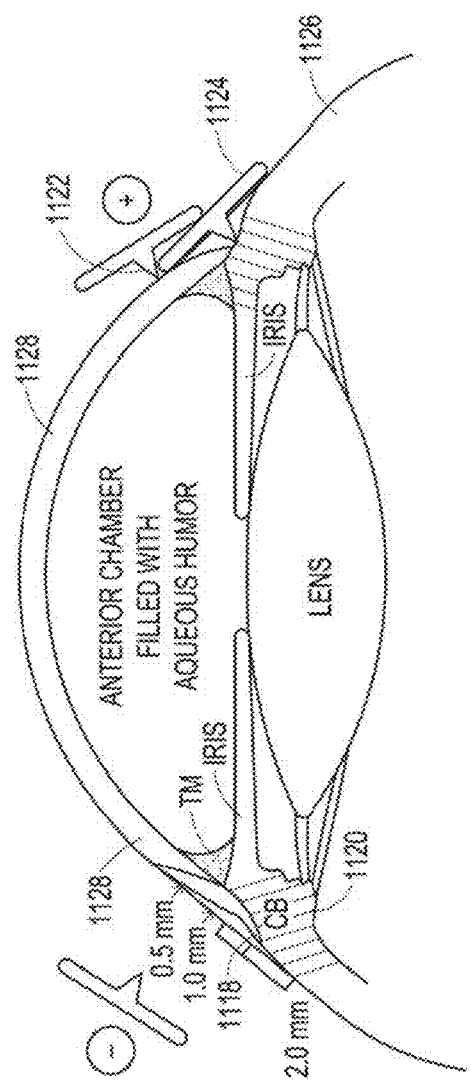
FIG. 12 depicts a cross-sectional side view of an eye and the placement of an electroporation system.

FIG. 12 illustrates an embodiment of the placement of the one, two, three, four, or five or more electrodes. Generally, the one, two, three, four, or five or more electrodes may be placed near a cornea sclera limbus junction 1128. In an embodiment, the one, two, three, four, or five or more electrodes may be disposed on a trabecular meshwork 1118. In an embodiment, the one, two, three, four, or five or more electrodes may be disposed a first distance 1122 from the trabecular meshwork 1118. In an embodiment, the one, two, three, four, or five or more electrodes may be disposed approximately 0.5 to 0.75 mm from the junction 1128, for example. In an embodiment, the one, two, three, four, or five or more electrodes may be disposed on a ciliary body 1120. In an embodiment, the one, two, three, four, or five or more electrodes may be disposed a second distance 1124 from the ciliary body 1120. In an embodiment, the one, two, three, four, or five or more electrodes may be disposed approximately 1.0 to 2.0 mm from the ciliary body 1120, for example, and above a sclera 1126.

Figure 11:
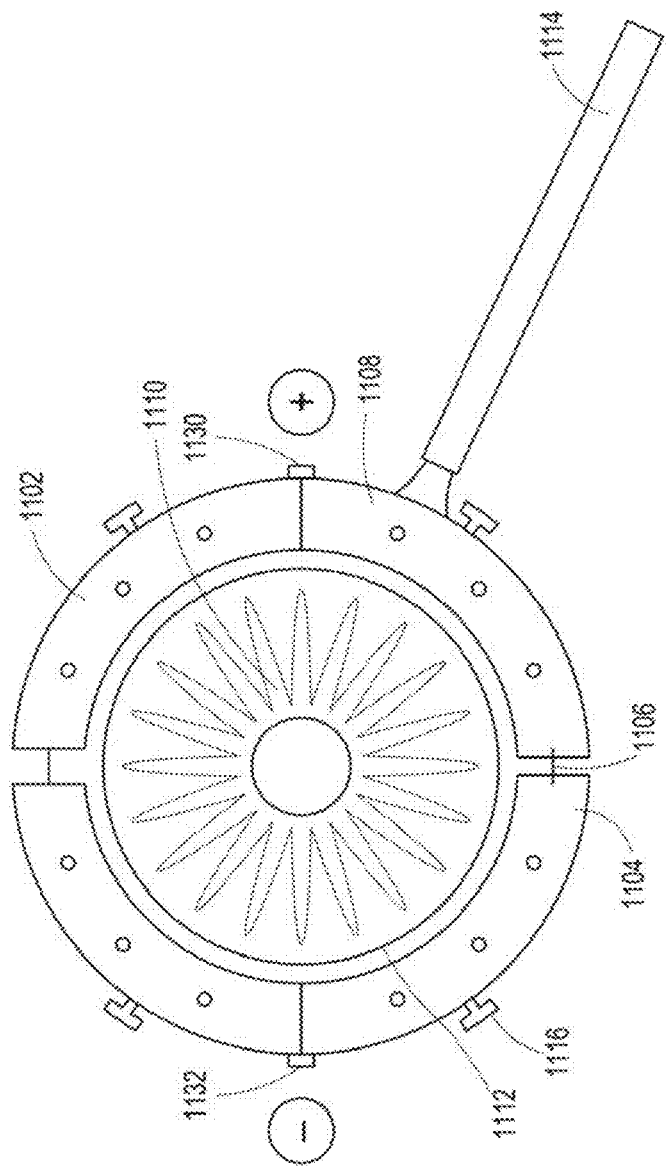
FIG. 11 is a schematic of a top view of an embodiment of an electroporation system.

FIG. 11 illustrates an embodiment of an electroporation system. An embodiment of the electroporation system may have an overall conical shape, cylindrical shape, and/or any other shape.

In an embodiment, the electroporation system is comprised of one, two, three, four, five or more electroporation plates. In an embodiment, each of the one, two, three, four, five or more electroporation plates can be tilted at an angle in an upwards direction to match a surface contour of the patient's eye. In an embodiment, each of the one, two, three, four, five or more electroporation plates may have a positive charge, a negative charge, and/or no electrical charge. In an embodiment, each of the one, two, three, four, five or more electroporation plates may have a positive terminal, a negative terminal, and/or no terminal for connecting cables to provide electric current. It is advantageous for each of the one, two, three, four, five or more electroporation plates disposed on opposite sides to have opposite electric charges to direct the flow of plasmids introduced into the eye.

For example, in FIG. 11, the electroporation system may comprise a first electroporation plate 1102 and a second electroporation plate 1104. In an embodiment, the first electroporation plate may have a positive terminal 1130 and the second electroporation plate may have a negative terminal 1132. In an embodiment, each of the first electroporation plate 1102 and the second electroporation plate 1104 can have a semi-circular shape and/or any other shape. For example, FIG. 6B illustrates a top view of an embodiment of the electroporation system. In an embodiment, the positively charged electroporation plate 502 and the negatively charged electroporation plate 504 may have a semi-circular shape, rectangular shape, circular shape and/or any other shape, In an embodiment, an electroporation housing 610 may be rectangular, semi-circular, circular and/or any other shape.

In an embodiment, each of the one, two, three, four, five or more electroporation plates may be divided into portions. For example, in FIG. 11, the first electroporation plate 1102 and the second electroporation plate 1104 are each divided into a first portion and a second portion to form quadrants. Each portion may comprise one, two, three, four, five or more electrodes 1108 for charging each of the one, two, three, four, five or more electroporation plates and/or for providing electric current to the eye. Advantageously, each quadrant, for example, may contain three, four, or five electrodes 1108. Each of the one, two, three, four, five or more electrodes 1108 may be connected by a wire within the one, two, three, four, five or more electroporation plates.

In an embodiment each of the one, two, three, four, or five or more electrodes 1108 may be disposable and/or replaceable. This would allow for more efficient treatment, as it would not be necessary to constantly sterilize the one, two, three, four, or five or more electrodes 1108. In an embodiment, an electrode switch 1116 may be coupled to an outer surface of each of the one, two, three, four, or five or more electroporation plates, which may be configured to engage or retract the one, two, three, four, or five or more electrodes 1108. In an embodiment, when each of the one, two, three, four, or five or more electrodes 1108 are in an engaged state, one, two, three, four, and/or five or more electrodes 1108 may be disposed beneath and/or under the surface of the electroporation plates and in contact with any portion of the eye (e.g., a cornea 1110) within a cornea sclera limbus junction 1112. In some embodiments, the one, two, three, four, or five or more electrodes 1108 may not be retractable.

As discussed above, it is advantageous for the one, two, three, four, or five or more electrodes 1108 of an embodiment of the electroporation system to contact the eye. Electroporation applies an electrical field to cells to increase the porosity of cell membranes. This allows DNA and/or drugs to be introduced into the cell. In embodiments, plasmids can be injected into the eye through the injection system 800. Thus, the electric current provided by the one, two, three, four, five, or more electrodes 1108 facilitates the introduction of the plasmids into the cells, thereby increasing the amount of a therapeutic gene of interest delivered to the target tissue. Additionally, electroporation may advantageously direct the flow of plasmid in the anterior chamber of the eye towards tissue, such as the trabecular meshwork to drain the eye. Further, the plasmids may be provided to the eye under constant and/or varying pressure and may be provided to the eye under high, medium, and/or low volume in some embodiments. Nonetheless, electroporation would allow the introduction of plasmids to be controlled.

In some embodiments, electroporation may be applied to a portion of the eye in one circumference of the eye. In other gene therapy methods for treating ocular disorders, treatment can be off-target and result in unwanted expressions in unwanted areas of the eye. Embodiments of the electroporation system and/or the injection system are advantageous because the expression formed by protein production can be controlled. In some embodiments, only a certain amount of protein generation is necessary. Applying electroporation to only a portion of the eye in one circumference of the eye could allow for concentrated protein generation in the particular area of the eye that should be treated.

In an embodiment, the first electroporation plate 1102 and the second electroporation plate 1104 can be adjustable. In an embodiment, a slide 1106 allows the first electroporation plate 1102 and the second electroporation plate 1104 to move about the slide 1106 and adjust the space between each electroporation plate. In other embodiments, the slide 1106 couples each of the one, two, three, four, five or more electroporation plates. This is advantageous because each of the electroporation plates are electrically charged and space between the electroporation plates would provide insulation. In addition, the slide 1106 is advantageous because the trabecular meshwork and shape of each patient's eye varies. In some embodiments, the slide 1106 would allow the electroporation system to be adjusted to the contours and shape of the patient's eye.

In some embodiments, a holder 1114 may be coupled to one, two, three, four, five and/or more of the electroporation plates. The holder 1114 may be insulated in an embodiment.

In an embodiment, the electroporation system may comprise an integrated injection system. In other embodiments, the injection system is not integrated with the electroporation system. In an embodiment, such as the embodiment illustrated in FIG. 5, the injection system passes vertically (either completely or partially) through the center (or a central portion) of the electroporation system. Advantageously, the syringe may pass through the electroporation system off-center and/or at an angle to prevent scarring and other potential side effects.

In several embodiments, the various parameters employed during electroporation can be tailored to a specific patient, a specific plasmid or other context specific characteristics that can be optimized to achieve a desired delivery of the plasmid DNA comprising a therapeutic gene to a target tissue, such as the trabecular meshwork. As discussed above, several embodiments of the electroporation device disclosed herein are adjustable to provide an optimized fit to the ocular surface for particular patient, in addition, in such embodiments wherein an arcuate electroporation device is employed, the arc (e.g. number of degrees) through which an electrical field is applied can be adjusted. In some embodiments, the entire circumference of the eye is simply divided into quadrants, with a positive electric field being applied to a first quadrant, and a negative electric field being applied to an opposite quadrant. In additional embodiments, smaller divisions around the entire circumference of the eye are used such as for example arcs of between about 1° to about 5°, about 5° to about 15°, about 15° to about 25°, about 25° to about 30°, about 30° to about 45°, about 45° to about 60°, about 60° to about 90°, and any arc in between those values listed, including endpoints. In some embodiments the variable arc is computer-controlled, such as, for example when an ocular scan or other diagnostic measure is performed in the resulting data are processed through a computer module. For example, diagnostic scan may be performed that reveals an optimal arc for electroporation of a particular value. In other embodiments, the variable arc is manually controlled and set by a physician based on previous experience with the patient, diagnostic evaluation, or the ordinary skill of the physician.

In some embodiments, the voltage used in electroporation ranges between about 50 millivolts (mV) to about 150 volts (V), including about 50 mV to about 75 mV, about 75 to about 100 mV, about 100 mV to about 150 mV, about 150 to about 200 mV, about 200 to about 250 mV, about 250 to about 300 mV, about 300 to about 350 mV, about 350 to about 400 mV, about 400 to about 450 mV, about 450 to about 500 mV, about 500 to about 550 mV, about 550 to about 600 mV, about 600 to about 650 mV, about 650 to about 700 mV, about 700 to about 750 mV, about 750 to about 800 mV, but 800 to about 850 mV, about 850 to about 900 mV, about 900 to about 950 mV, about 950 mV to about 1 V, about 1 to about 5 V, about 5 to about 10 V, about 10 to about 15 V, about 15 to about 20 V, about 20 to about 25 V, about 25 to about 30 V, about 30 to about 35 V, about 35 to about 40 V, about 40 to about 45 V, about 45 to about 50 V, about 50 to about 55 V, about 55 to about 60 V, about 60 to about 65 V, about 65 to about 70 V, about 70 to about 75 V, about 75 to about 80 V, about 80 to about 85 V, about 85 to about 90 V, about 90 to about 95 V, about 95 to about 100 volts, about 100 to about 110 V, about 110 to about 120 V, about 120 to about 130 V, about 130 to about 140 V, about 140 to about 150 V, and any voltage in between those listed, including endpoints.

The number of pulses applied to the ocular surface in a given electroporation session may range from between about two pulses to about 20 pulses including, 2 to 3 pulses, 3 to 4 pulses, 4 to 5 pulses, 5 to 6 pulses, 6 to 7 pulses, 7 to 8 pulses, 8 to 9 the pulses, 9 to 10 pulses, 10 to 12 pulses, 12 to 14 pulses, 14 to 16 pulses, 16 to 18 pulses, or 18 to 20 pulses. Depending on the embodiment a greater number of pulses may also be used.

The duration of the pulses applied to the ocular surface in a given electroporation session can range between about 0.5 milliseconds (ms) to about 10 ms, including about 0.5 to about 1 ms, about 1 to about 2 ms, about 2 to about 3 ms, about 3 to about 4 ms, about 4 to about 5 ms, about 5 to about 6 ms, about 6 to about 7 ms, about 7 to about 8 ms, about 8 to about 9 ms, or about 9 to about 10 ms, or any time in between those times listed including endpoints.

Intervals between the applied pulses can also vary depending on the embodiment. Pulse intervals can be between about 20 ms and about 200 ms, including about 20 to about 30 ms, about 30 to about 40 ms, about 40 to about 50 ms, about 50 to about 60 ms, about 60 to about 70 ms, about 70 to about 80 ms, about 80 to about 90 ms, about 90 to about 100 ms, about 100 to about 110 ms, about 110 to about 120 ms, about 120 to about 130 ms, about 130 to about 140 ms, about 140 to about 150 ms, about 150 to about 170 ms, about 170 to about 190 ms, about 190 to about 200 ms, or any time in between those listed including endpoints.

The pulse train can vary as well, depending on the embodiment. In some embodiments the pulse train ranges from 1 to 10, including from 1 to 2, from 2 to 3, from 3 to 4, from 4 to 5, from 5 to 6, from 6 to 7, from 7 to 8, from 8 to 9, from 9 to 10 or any value in between, including endpoints. As discussed herein, the amount of DNA delivered in conjunction with electric ration can also be adjusted. For example, in some embodiments the plasmid DNA concentration ranges from about 0.1 to about 20 µg in a volume of between about 1 and about 300 µL. More specifically, the amount of DNA can range from about 0.1 µg to about 1 µg, about 1 µg to about 2 µg, about 2 µg to about 3 µg, about 3 µg to about 4 µg, about 4 µg to about 5 µg, about 5 µg to about 6 µg, about 6 µg to about 7 µg, about 7 µg to about 8 µg, about 8 µg to about 9 µg, about 9 µg to about 10 µg, about 10 µg to about 12 µg, about 12 µg to about 14 µg, about 14 µg to about 16 µg, about 16 µg to about 18 µg, about 18 µg to about 20 µg, and any amount of plasmid DNA in between those values listed, including endpoints. Depending on the volume of plasmid DNA being delivered and the volume of the anterior chamber of a particular subject, the amount of DNA can be greater, in some embodiments. Additionally, the volume of the plasmid DNA solution can, depending on the embodiment, range from about 1 µL to about 2 µL, about 2 µL, to about 2.5 µL, about 2.5 µL, to about 3 µL, about 3 µL, about 3.5 µL, about 3.5 µL, to about 4 µL, about 4 µL, to about 4.5 µL, about 4.5 µL, to about 5 µL, about 5 µL, to about 6 µL, about 6 µL, to about 7 µL, about 7 µL, about 8 µL, about 8 µL, to about 9 µL, about 9 µL, about 10 µL, about 10 µL, to about 12 µL, about 12 µL, to about 14 µL, about 14 µL, about 16 µL, about 16 µL, to about 18 µL, about 18 µL, to about 20 µL, about 20 µL, to about 25 µL, about 25 µL, to about 30 µL, about 30 µL, to about 35 µL, about 35 µL, to about 40 µL, about 40 µL, to about 45 µL, about 45 µL, to about 50 µL, about 50 µL, to about 100 µL, about 100 µL, to about 150 µL, about 150 µL, to about 200 µL, about 200 µL, to about 250 µL, about 250 µL, to about 300 µL, and any volume in between those listed. Additionally, as discussed herein, depending on other characteristics (e.g. the amount of plasmid DNA to be delivered, the volume of the anterior chamber of a particular subject, etc.) greater volumes can also be used. In still further embodiments, the devices disclosed herein can advantageously be used to increase the concentration of plasmid DNA through a process of withdrawal of fluid from the anterior chamber followed by replacing that fluid with plasmid DNA solution. For example, once accessing the interior chamber a withdrawal syringe can remove, for example 25 to 50 µL of ocular fluid (that ocular fluid having no plasmid DNA contained within it). The removed fluid volume can then be replaced with a treatment solution comprising plasmid DNA. By repeating this withdrawal an injection procedure multiple times, the ultimate concentration of plasmid DNA can be increased, to the point where the entire fluid volume of the anterior chamber is made up of treatment solution comprising plasmid DNA.

Depending on the placement of the electrodes, whether individual electrodes or arcuate electrodes are used, the plane of the electric field applied during electroporation can be targeted to specific ocular tissues. As discussed above, in some embodiments the plane of the electric field is focused on the trabecular meshwork. In additional embodiments, the plane of the electric field is shifted to focus on the ciliary body. In still additional embodiments, the plane of the electric field is shifted to focus on limbus and/or the posterior globe of the eye.

Figure 13:
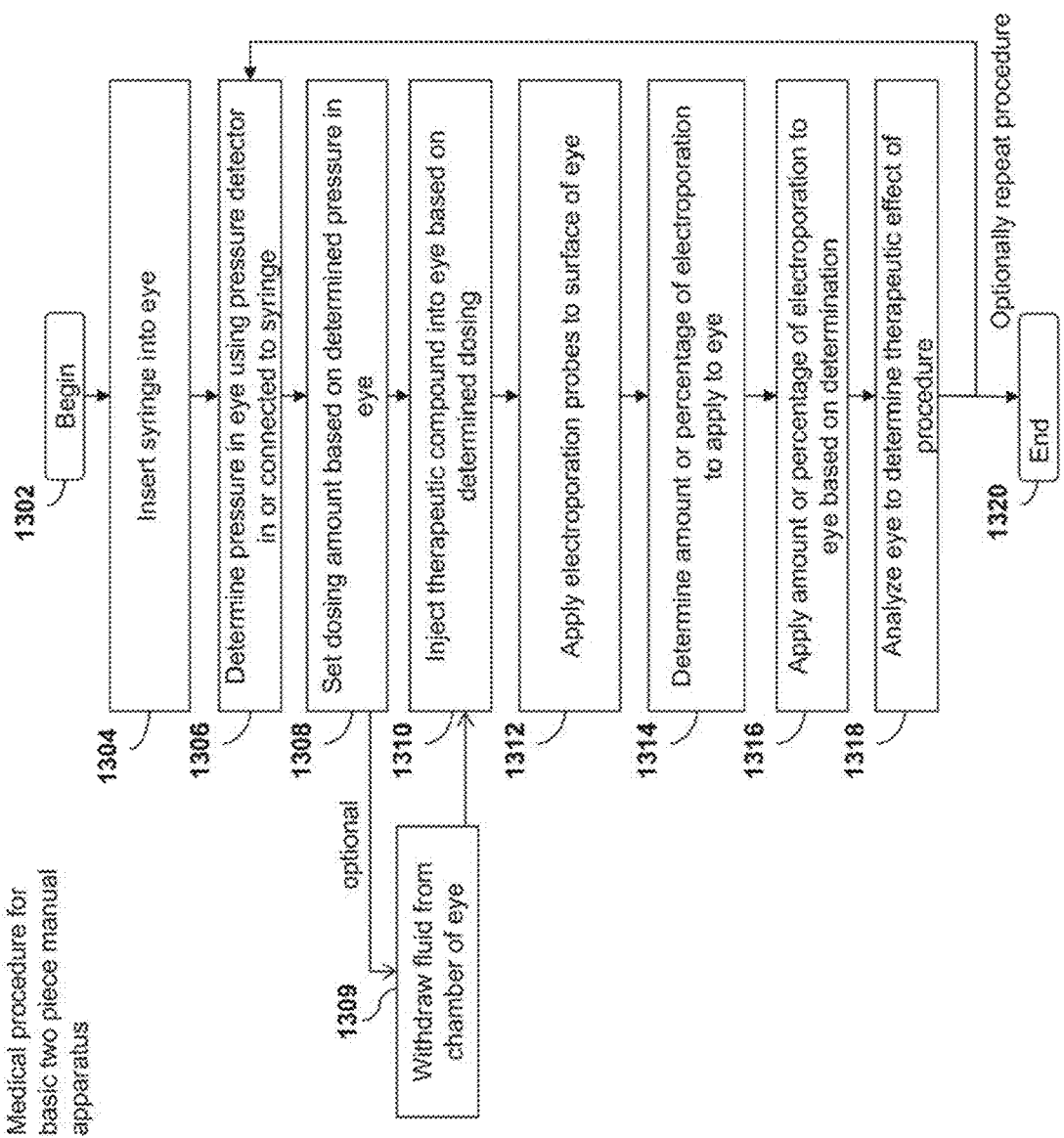
FIG. 13 is a flow chart depicting an embodiment of a medical procedure for a two piece manual system.

FIG. 13 is a flow chart depicting an embodiment of a medical process for a treatment system comprising a two piece manual system. In an embodiment, the process can start at block 1302. At block 1304, a syringe can be inserted into the patient's eye. At block 1306, a pressure in the eye can be determined by using a pressure detector in and/or connected to the syringe. In an embodiment, the pressure may be seen on a display of the pressure detector. In an embodiment, the pressure may be seen on a display of the treatment system. In an embodiment, pressure readings may be used to guide plasmid delivery at a predetermined pressure. As mentioned above, this process can also optionally include a series of consecutive withdrawal and infusion actions (see optional block 1309—while not shown, corresponding optional blocks are present in the procedures shown in FIGS. 14 and 15). That is, ocular fluid from the anterior chamber can be withdrawn and replaced with a treatment solution comprising plasmid DNA. In some embodiments, the monitor pressure assists an operator in maintaining a desirable window of pressure during the withdrawal and/or infusion process, thereby reducing potential damage to intraocular tissue. By virtue of a repeated withdraw and infusion process, the concentration of plasmid DNA delivered to the anterior chamber can be elevated.

At block 1308, a dosing amount can be set based on the pressure determined at block 1306. In an embodiment, the dosing amount can be set on a dial and/or connected to the syringe. At block 1310, the therapeutic compound can be injected into the eye based on the dosing determined at block 1306. At block 1312, a one or more electroporation probes may be applied to a surface of the eye. At block 1314, an amount (e.g., a volume or a percentage) of electroporation can be determined to apply to the eye. At block 1316, the amount of electroporation as determined at block 1314 can be applied to the eye. As discussed in more detail herein, the time that separates DNA delivery in the application of electric field can vary, depending on the embodiment. The variation in the time between delivery and application of electric field may be dictated, in some embodiments by the amount of plasmid DNA being delivered and or the concentration within the anterior chamber (for example as a result of the withdrawal infusion procedure described above). In still additional embodiments that employ a withdraw and infusion procedure, electroporation can optionally be applied after each injection of plasmid DNA. Alternatively once a desired amount of plasmid DNA has been delivered to the anterior chamber, then a single application of electric field can be used.

At block 1318, the eye can be analyzed to determine the therapeutic effect of the process. Depending on the therapeutic effect, the process can be repeated starting at block 1306. If the process may not be repeated, at block 1320, the process can be completed.

Figure 14:
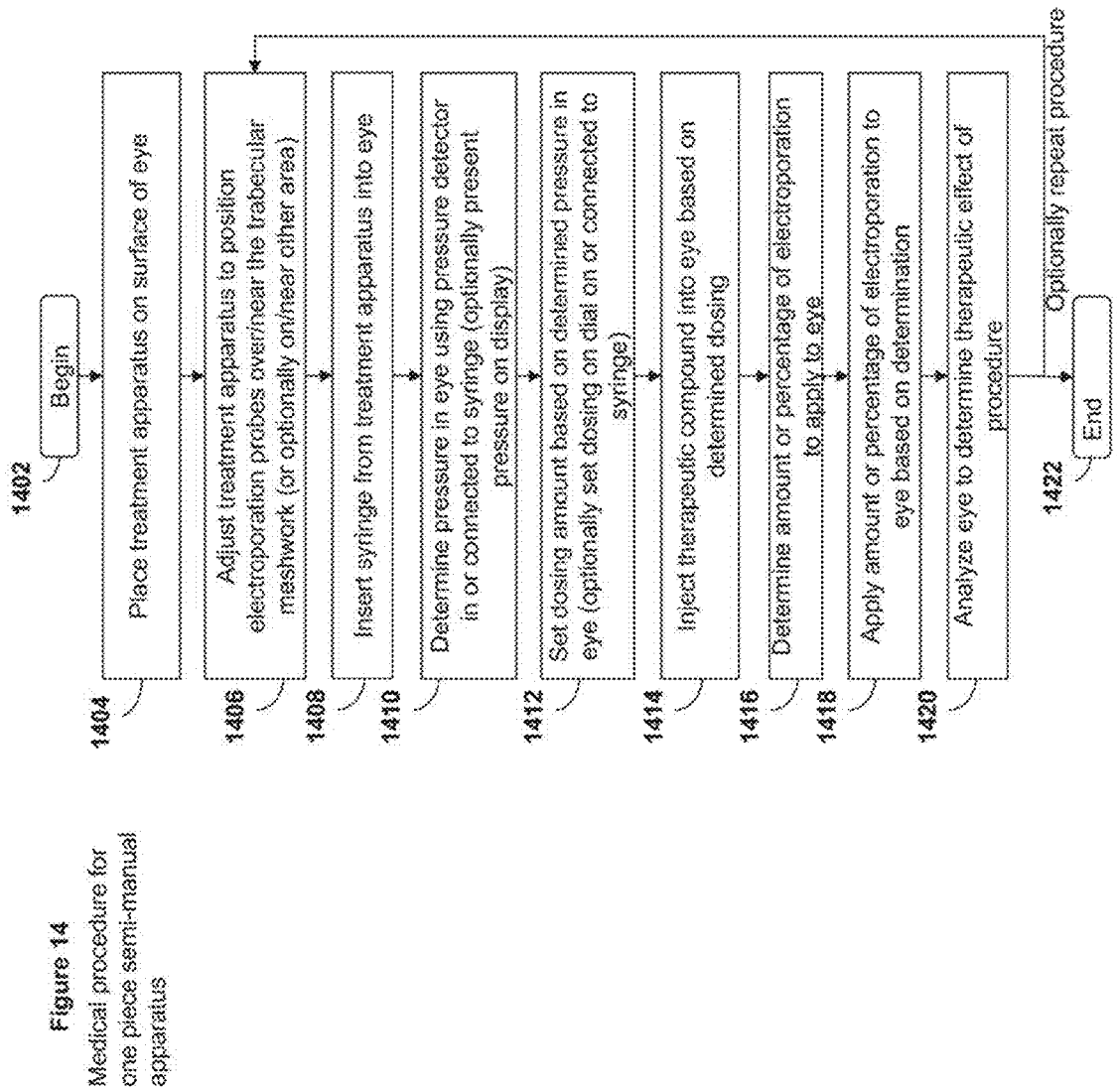
FIG. 14 is a flow chart depicting an embodiment of a medical procedure for a one piece semi-manual system.

FIG. 14 is a flow chart depicting an embodiment of a medical process for a treatment system comprising a one piece semi-automatic system. In an embodiment, the process can start at block 1402. At block 1404, the treatment system can be placed on the surface of the patient's eye. At block 1406, the treatment system can be adjusted to position one or more electroporation probes over and/or near the trabecular meshwork. In an embodiment, the treatment system can be adjusted to position one or more electroporation probes over and/or near other portions of the eye.

At block 1408, a syringe from the treatment system may be inserted into the eye. At block 1410 a pressure in the eye can be determined by using a pressure detector in and/or connected to the syringe. In an embodiment, the pressure may be seen on a display of the pressure detector. In an embodiment, the pressure may be seen on a display of the treatment system.

At block 1412, a dosing amount can be set based on the pressure determined at block 1410. In an embodiment, the dosing amount can be set on a dial and/or connected to the syringe. At block 1414, the therapeutic compound can be injected into the eye based on the pressure determined at block 1410. At block 1416, an amount (e.g., a volume or a percentage) of electroporation can be determined to apply to the eye. At block 1418, the amount of electroporation as determined at block 1416 can be applied to the eye.

At block 1420, the eye can be analyzed to determine the therapeutic effect of the process. Depending on the therapeutic effect, the process can be repeated starting at block 1406. If the process may not be repeated, at block 1422, the process can be completed.

Figure 15:
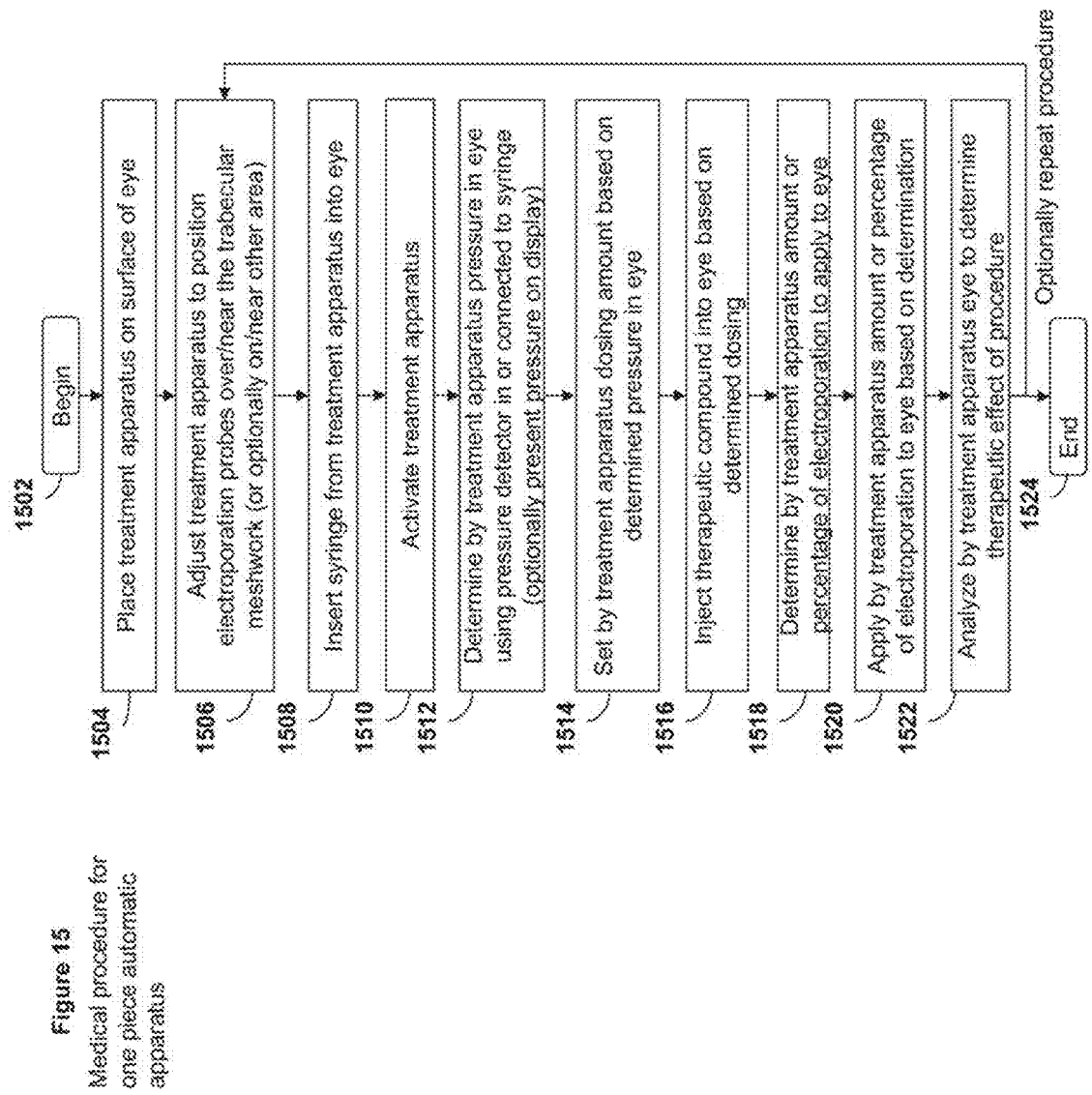
FIG. 15 is a flow chart depicting an embodiment of a medical procedure for a one piece automatic system.

FIG. 15 is a flow chart depicting an embodiment of a medical process for a treatment system comprising a one piece automatic system. In an embodiment, the process can start at block 1502. At block 1504, the treatment system can be placed on the surface of the patient's eye. At block 1506, the treatment system can be adjusted to position one or more electroporation probes over and/or near the trabecular meshwork. In an embodiment, the treatment system can be adjusted to position one or more electroporation probes over and/or near other portions of the eye.

At block 1508, a syringe from the treatment system may be inserted into the eye. At block 1510, the treatment system may be activated. At block 1512, the treatment system can determine a pressure in the eye by using a pressure detector in and/or connected to the syringe. In an embodiment, the pressure may be seen on a display of the pressure detector. In an embodiment, the pressure may be seen on a display of the treatment system.

At block 1514, the treatment system can set a dosing amount based on the pressure the treatment system determined at block 1512. At block 1516, the therapeutic compound can be injected into the eye based on the pressure determined at block 1512. At block 1518, the treatment system can determine an amount (e.g., a volume or a percentage) of electroporation to apply to the eye. At block 1520, the treatment system can apply the amount of electroporation as determined at block 1518.

At block 1522, the treatment system can analyze the eye to determine the therapeutic effect of the process. Depending on the therapeutic effect, the process can be repeated starting at block 1506. If the process may not be repeated, at block 1524, the process can be completed.

Delivery

Depending on the embodiment, delivery of plasmid DNA comprising a therapeutic gene can be by with one or more of a variety of routes. Selection of the route may depend on the target tissue to be treated, the particular characteristics of the patient (e.g., the patient's current health status at the time of treatment), the particular characteristics of the plasmid DNA and or therapeutic gene to be delivered (e.g., in the tissue specific promoter used, such that an indirect delivery route can be effective), or on other variables discussed herein. According to several embodiments, delivery can be by intravenous infusion, intra-arterial infusion, intramuscular injection, subcutaneous injection, direct injection to a target tissue, delivery of the plasmid DNA to an orifice or chamber in communication with a target tissue, topically, orally, nasally, delivery to one or more mucous membranes, etc. In certain embodiments, delivery of the plasmid DNA is by injection, using one or more of the devices disclosed herein, to deliver the plasmid DNA to the anterior chamber of the eye of a subject. Because the trabecular meshwork serves as the primary gatekeeper of outflow of ocular fluid from the anterior chamber, delivery of the plasmid DNA to the anterior chamber results in uptake of the plasmid DNA by the cells of the trabecular meshwork, and subsequent expression of the therapeutic gene in those cells of the trabecular meshwork.

Various carriers can be used to facilitate the delivery of the plasmid DNA comprising a therapeutic gene such as parentheses phosphate buffered saline, normal saline, Hank's Balanced Salt Solution, Krebs buffer, ocular fluid (either synthetic or natural), or any other of a variety of suitable carriers that are compatible with intraocular delivery.

Depending on the embodiment, the methods, devices and systems disclosed herein can be used in delivering plasmid DNA comprising a therapeutic gene to a patient in a clinic setting (e.g. an outpatient environment). In some embodiments, delivery of therapeutic plasmid DNA can be performed over a longer time course, as described below, for example in a surgical suite environment. The choice of delivery method and time as discussed above they depend on the characteristics of the patient and/or the particular plasmid DNA being delivered.

Delivery parameters can be varied depending upon a particular subject and his or her physical characteristics among other considerations disclosed herein. In some embodiments, the frequency of injection (or infusion) of the plasmid DNA can range from delivery every few weeks to delivery only once or twice per year, or even less frequently. For example, delivery can be once every two weeks, once every three weeks, once every four weeks, once every six weeks, once every eight weeks, once every 12 weeks, once every 16 weeks, once every 20 weeks, or once every 24 weeks (or at any delivery interval in between those listed, including endpoints). In some embodiments, delivery is targeted to be once or twice every 1-2 years.

Depending on the gene of interest, and/or the target cell population, among other considerations, the duration of efficacy (e.g. how long the therapeutic gene of interest is expressed) may vary from several weeks to several months, or even up to several years, depending on the embodiment. For example, in some embodiments, after delivery, the therapeutic gene of interest is expressed for at least three weeks, at least about four weeks, at least about six weeks, at least about eight weeks, at least about 12 weeks, at least about 16 weeks, at least about 20 weeks, at least about 24 weeks, at least about 12 months, at least about 18 months, or at least about 24 months (or any duration in between those listed, including endpoints).

Delivery volume will depend, in some embodiments, on the patient being treated (e.g. a child versus an adult), but will generally range between about 10 to about 1000 µL, including about 10 to about 20 µL, about 20 to about 30 µL, about 30 to about 40 µL, about 40 to about 50 µL, about 50 µL, to about 100 µL, about 100 µL, to about 125 µL, about 125 µL, to about 150 µL, about 150 µL, to about 175 µL, about 175 µL, to about 200 µL, about 200 µL, to about 250 µL, about 250 µL, to about 300 µL, about 300 µL, to about 350 µL, about 350 µL, to about 400 µL, about 400 µL, to about 450 µL, about 450 µL, to about 500 µL, about 500 µL to about 600 µL, about 600 µL to about 700 µL, about 700 µL to about 800 µL, about 800 µL to about 900 µL, about 900 µL to about 1000 µL, or any volume in between those listed including endpoints.

The rate of delivery of the therapeutic plasmid DNA will vary depending on the embodiment, e.g., an injection in an outpatient clinic versus a longer duration perfusion, for example performed in a surgical suite or operating room. The volume of the therapeutic plasmid DNA being delivered will also impact the rate of delivery. However in some embodiments rate of delivery will range between about 1 to about 3 seconds, about 3 to about 6 seconds, about 6 to about 10 seconds, about 10 to about 15 seconds, or about 15 to about 20 seconds (or any time in between those listed including endpoints). Longer injection times may also be used, for example on the order of about 30 to 60 seconds, depending on the embodiment. In those embodiments where the therapeutic plasmid DNA is delivered by perfusion, the duration of perfusion can range from about 5 to about 90 minutes including about five to about six minutes, about six to about seven minutes, about seven to about eight minutes, about eight to about nine minutes, about nine to about 10 minutes, about 10 minutes to about 20 minutes, about 20 minutes to about 30 minutes, about 30 minutes to about 40 minutes, about 40 minutes to about 50 minutes, about 50 minutes to about 60 minute, about 60 minutes to about 70 minutes, about 70 minutes to about 80 minutes, about 80 minutes to about 90 minutes, or any time in between those times listed, including endpoints. In some embodiments the longer infusion time is beneficial because the target cells, e.g. the trabecular meshwork, are not overrun by an excess of plasmid DNA that could reduce the ultimate transfection efficiency of the trabecular meshwork cells.

Depending on the embodiment, delivery of the plasmid DNA can be at a constant rate or at a variable rate. For example, a constant rate of delivery can range from about 0.25 µL per minute to about 30 µL per minute, including about 0.25 µL per minute to about 0.5 µL per minute, about 0.5 µL per minute to about 1 µL per minute, about 1 µL per minute to about 2 µL per minute, about 2 µL per minute to about 4 µL per minute, about 4 µL per minute to about 8 µL per minute, about 8 µL per minute to about 10 µL per minute, about 10 µL per minute to about 15 µL per minute, about 15 µL per minute to about 20 µL per minute, about 20 µL, per minute to about 25 µL, per minute, about 25 µL, per minute to about 30 µL, per minute, and any value in between those listed, including endpoints.

In those embodiments wherein a variable rate is used, the rate can be adjusted, for example, in real time to accommodate the increased pressure that can occur through the delivery of a plasmid DNA containing solution to the anterior chamber of the eye (or another target tissue), as well as adjusting in a real-time (or moment-to-moment basis) to account for fluctuations in the intraocular pressure of a the eye of a subject.

Depending on the embodiment, the pressure of delivery of the therapeutic agent can be varied to account for the current pressure in the eye of a given subject. For example, a patient who is in the early stages of an ocular disease may have only slightly elevated intraocular pressure may have only slightly elevated intraocular pressure and can tolerate higher pressure of delivery of a therapeutic agent without risking pressure induce damage to sensitive intraocular tissues. In contrast, other patients may have a more advanced disease state that is associated with significantly elevated intraocular pressure, and therefore the additional pressure imparted by delivery of the therapeutic agent cannot be as great without risk of damaging sensitive intraocular tissues. Thus, the pressure at which the therapeutic agent is delivered in accordance with several embodiments can vary between about 10 millimeters of mercury (mm Hg) to about 50 mmHg. For example, the pressure at which the therapeutic agent is delivered can range from about 10 to about 15 mmHg, from about 15 to about 20 mmHg, from about 22 about 25 mmHg, from about 25 to about 30 mmHg, from about 30 to about 35 mmHg, from about 35 to about 40 mm Hg, from about 45 to about 50 mmHg, and any pressure in between those listed above, including endpoints.

In addition to the other variables disclosed herein, the amounts or concentration of plasmid DNA within the therapeutic agent delivered can vary from subject to subject. For example, in some embodiments the target range of DNA copies that are introduced into the nucleus of a given target cell (e.g., trabecular meshwork cell) is between 50 and 50,000 copies. However, it should be appreciated that not all therapeutic genes are expressed as efficiently as others. Therefore, the concentration can be varied depending on the desired expression level of a given therapeutic gene. Taking this into account, one can also select a particular promoter to maximize expression levels of a therapeutic gene of interest. In some embodiments, the number of copies of the DNA sequence of interest ranges from about 1000 copies per nucleus to about 5000 copies per nucleus, including about 1000 to about 2000 copies per nucleus, about 2000 to about 3000 copies per nucleus, about 3000 about 4000 copies per nucleus, about 4000 about 5000 copies per nucleus, and any amount in between, including endpoints. It should be appreciated that this concentration can be varied readily using ordinary skill in the art, based on the guidance provided in the present disclosure, to achieve desired therapeutic efficacy.

The amount of plasmid DNA (including the therapeutic gene of interest) delivered to the anterior chamber of the eye of subject (or other target location) can vary, depending on the embodiment. The amount can be between about 0.1 micrograms (µg) and about 10 µg, including about 0.1 to about 0.5 µg, about 0.5 to about 1.0 µg, about 1.0 to about 1.5 µg, about 1.5 to about 2.0 µg, about 2.0 to about 2.5 µg, about 2.5 to about 3.0 µg, about 3.0 to about 3.5 µg, about 3.5 to about 4.0 µg, about 4.0 to about 4.5 µg, about 4.5 to about 5.0 µg, about 5.0 to about 7.5 µg, about 7.5 to about 10.0 µg and any amount between those listed, including endpoints.

While, in some instances, tissue transfection with plasmid may be less efficient than desired, in accordance with several embodiments, hydrodynamically perfusing pDNA into the isolated anterior chamber compartment increases the efficiency of transfection of the cells of the trabecular meshwork. In addition, in several embodiments, when combined with electroporation, the efficiency of plasmid transfection of the trabecular meshwork is significantly increased.

The plasma membrane is a lipid barrier separating the intracellular and extracellular spaces. Exogenous genes or DNA and many drugs that are deposited in the extracellular space cannot cross this barrier to enter the cell. The intracellular and extracellular spaces are filled with ionically conductive fluid. In an electric field, ions in the intracellular and extracellular spaces move by electrophoresis but are impeded by the plasma membrane from crossing from one space into the other. Instead, oppositely charged particles accumulate on each side of the plasma membrane. This generates a potential difference across the plasma membrane. Electroporation occurs above a threshold potential difference wherein transient structural changes occur in the plasma membrane to alter membrane conductivity and permeability. By varying the parameters of electrical stimulation (e.g., field strength, pulse duration, number of pulses), it is possible to modulate certain characteristics of membrane permeability, thereby providing a measure of control over the transfection process, as is described herein in accordance with several embodiments. Electrical stimulation parameters may also be varied to determine cellular recovery and viability after electroporation. These characteristics make electroporation-assisted gene therapy an attractive proposition. The electrically-induced change in membrane barrier function is attributed to transient opening of membrane pores. It is believed that these membrane pores are hydrophobic initially, but subsequently membrane lipids rearrange to render pores hydrophilic. This facilitates transmembrane transfer of ions and molecules. DNA itself is highly charged and directable, as it may be made to move along the vector of an electrical field during electroporation.

Figures 24A, 24B:
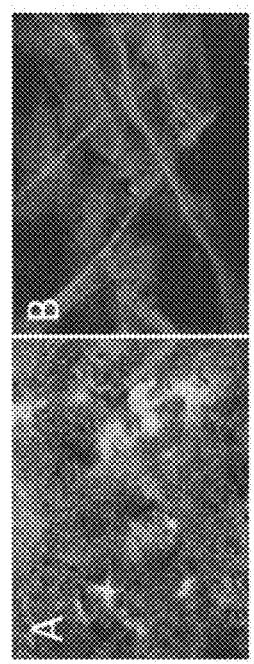
FIG. 24A-24B depict experimental data regarding LOXL1 expression. 24A depicts an embodiment of transgenic LOXL1 expression amongst elastin aggregates lacking fibrils in LOXL1 mouse TM after pDNA perfusion. 24B depicts an embodiment of fibrillary elastin in WT negative control mouse.

The TM lies immediately adjacent to the ocular surface externally and anterior chamber internally. The TM is bathed by aqueous humor. Aqueous humor, being a physiological salt solution, serves as an excellent ionic conductor, as evidenced during electroporation of the adjacent cornea. The aqueous-filled anterior chamber represents a depot into which a gene or DNA may easily be deposited by transcorneal injection. Within this space, exogenous DNA mixes with aqueous humor to then bathe TM cells in a way that enhances gene delivery when coupled with TM electroporation. The TM, being immediately adjacent to the ocular surface, is accessible by surface electrodes that are used to generate an electric field across the tissue. This makes the position of the TM in the anterior eye ideal for minimally invasive electroporation-assisted gene delivery and transfection. Electroporation to transfect human TM in the absence of viral vectors, is shown in FIG. 24A-24B.

EXAMPLES

Figure 16:
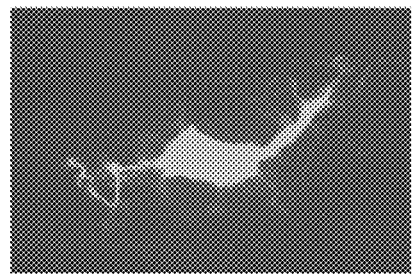
FIG. 16 is an image of an embodiment of a single TM cell expressing GFP.

Example 1—Electroporation-Assisted Delivery of Nucleic Acid to the Trabecular Meshwork This example relates to non-viral electroporation-assisted transfection as a way of delivering genes to the trabecular meshwork (TM). As discussed above, the TM lies immediately adjacent to the ocular surface externally and anterior chamber internally. The TM is bathed by aqueous humor. Aqueous humor, being a physiological salt solution, serves as an excellent ionic conductor. The aqueous-filled anterior chamber represents a depot into which a gene or DNA may be deposited by trans-corneal injection, perfusion, etc., as is disclosed above. Within this space, exogenous DNA mixes with aqueous humor to then bathe TM cells. To facilitate delivery of the gene of interest to the TM cells, application of an electric field can be used. The TM, being immediately adjacent to the ocular surface, is readily accessible by surface electrodes that are used to generate an electric field across the tissue, thereby making the position of the TM in the anterior eye particular attractive for minimally invasive electroporation-assisted gene delivery and transfection. Preliminary data, shown in FIG. 16, indicate that electroporation can be used to transfect human TM in the absence of viral vectors.

Figures 17A, 17B, 17C:
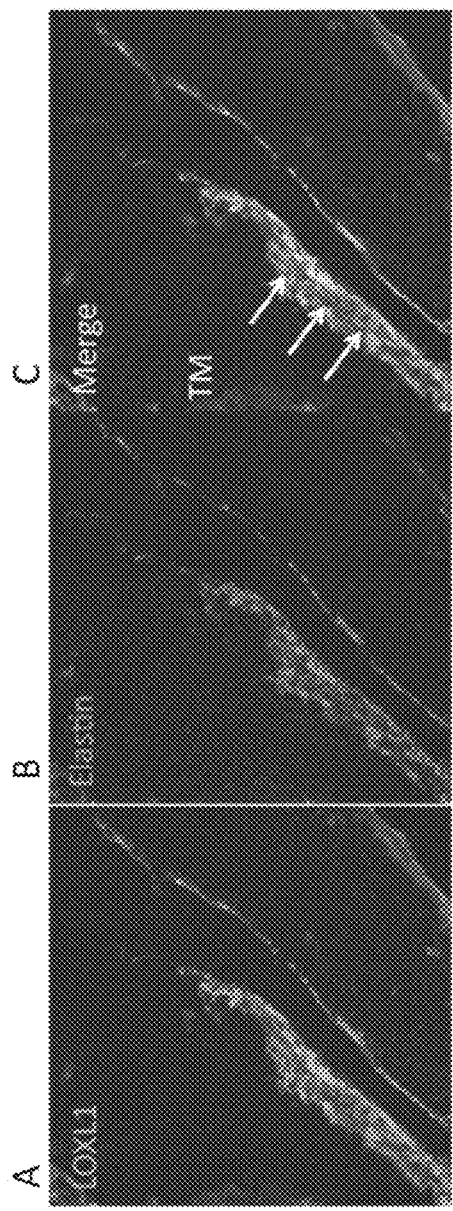
FIGS. 17A-17C depict an embodiment of immunohistochemistry.

To determine the efficacy of supplementing delivery of plasmid DNA with electroporation, a plasmid DNA vector with/without a LOXL1 gene will be delivered to the TM of wild-type C57BL/6 and LOXL1$^{-/-}$ mice. Wild-type (WT) C57BL/6 mice express abundant LOXL1 and elastin in the TM, as shown in FIGS. 17A-17C. FIG. 17A shows the expression of LOXL1, 17B the expression of elastin, and 17C the co-localization of those two genes. This expression pattern contrasts with LOXL1−/− mice that are deficient in LOXL1. Effect and efficiency of in vivo electroporation-assisted LOXL1 transfection will then be assessed.

Materials and Methods

Mouse LOXL1 Cloning

The full-length cDNA coding sequence of the mouse LOXL1 gene (cDNA 3.15 kbp; clone #MC203207 (OriGene); NM_010729) will be cloned into a commercially-available mammalian expression vector with DsRed2 red fluorescent reporter downstream from a CMV promoter (pDsRed2-N1; Clontech; Cat #632406). The vector with LOXL1 gene (pDsRed2-N1.LOXL1) will be amplified and purified using an endotoxin-free kit.

LOXL1 Transfection by Anterior Chamber Perfusion Alone

Figures 18A, 18B:
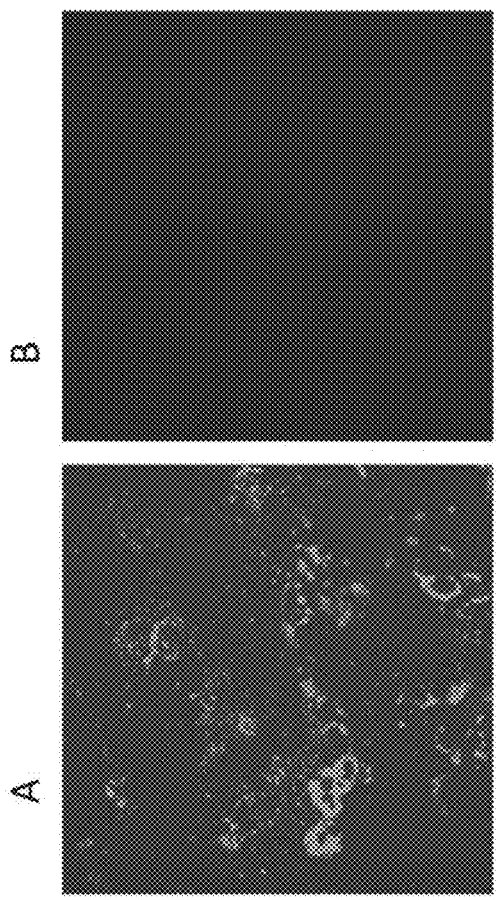
FIGS. 18A-18B depicts DsRed2 plasmid-mediated expression in cells of the trabecular meshwork (A) but not in control tissue receiving vehicle only without plasmid (B) after anterior chamber delivery in vivo.

The plasmid DNA vector with or without LOXL1 will be delivered into the mouse anterior chamber by perfusion. WT C57BL/6 mice aged 8-12 weeks (w) will be used. Initially, optimization experiments will be performed in which the empty pDsRed2-N1 vector will be perfused alone in WT mice. Subsequently, pDsRed2-N1.LOXL1 will be perfused in WT mice. Different parameters will be tested to optimize transfection efficiency, including, but not limited to, volume of solution perfused; perfusion rate and duration; and DNA dose, among others. Different doses of pDsRed2-N1 vector and pDsRed2-N1.LOXL1 (0.1-10 µg) will be diluted in different volumes (2.5, 5, 10, 20 µL of PBS) and perfused at different constant flow rates (0.25, 0.5, 1, 2, 4 µL/min) for different durations (30 s, 1, 2, 4 min), as volume and flow rate may influence transfection efficiency. Longer duration perfusions (30, 60 min) will also be performed at flowrates of 0.25, 0.5 and 1 µL/min. Transfection efficiency and transgene expression will be assessed in flat mount and immunohistochemistry (FIG. 18A-18B) 24-48 h after gene delivery.

Electroporation-Assisted LOXL1 Transfection in Wild-Type Mice

Once an optimal strategy for TM transfection by perfusion alone (of pDsRed2-N1 and pDsRed2-N1.LOXL1, as examples of plasmid DNA that can be delivered) has been determined in WT mice, this protocol will be repeated under the influence of electroporation. Eyes will be electroporated immediately after anterior chamber gene perfusion (though in some embodiments disclosed above, electroporation occurs coincident with administration). Electroporation will be performed using tweezer electrodes (20 G platinum-iridium loops with tips or pads) on a BTX ECM 830 electroporator (Harvard Apparatus, MA). The mouse will be anesthetized with a ketamine/xylazine/acepromazine cocktail administered intraperitoneally and positioned on its side under a body warmer. With the eyelids separated and gentle pressure exerted in the mouse periorbital area to prolapse the globe slightly and expose the mouse limbal region, the electrode tips (anode and cathode) will be placed 180 degrees apart and in contact with sclera overlying the TM. Once electrodes are correctly positioned, a foot pedal will be depressed to apply current according to preset parameters. Care will be taken to avoid electrode-electrode contact during electroporation.

A protocol optimizing electroporation-assisted LOXL1 transfection of the live mouse TM will be determined. Starting ranges for electroporation will be: (a) voltage 5-80V, (b) 5-10 pulses, (c) 1-5 ms pulse duration, (d) 50-100 ms pulse intervals, (e) 1-3 pulse train, and (f) DNA concentration of 0.1-10.0 µg in 2.5-20 µL. Transfection efficiency will be compared with controls receiving transfection by perfusion only. Fellow unperfused eyes and separate untransfected WT mice will serve as negative controls. Possibility of electrically-induced tissue or cellular damage will be assessed by hemotoxylin and eosin (H&E) and TUNEL staining. Combined findings will be used to guide the fine-tuning of electroporation parameters.

After electroporation, mice will be recovered under a warming blanket in a clean cage until they wake and start moving (1-2 h). Artificial tears will be administered to the cornea every 5-10 minutes to prevent drying. Transfection efficiency and transgene tissue localization will be assessed 24-48 h after gene delivery in anterior segment flat mounts and by immunohistochemistry. The different fluorophores of (a) DSRed2 (vector) and (b) LOXL1 (antibody-labeled; Alexa-488) will be assessed and distinguished by confocal microscopy. Quantitative fluorescence profiling will be performed in the TM by established methods.

Longevity of expression will be assessed 1 w, 1 m, 3 m and 6 m after transfection. Transgene expression in the downstream aqueous outflow tract (Schlemm's canal, collector channels, episcleral veins) will be ascertained in radial histological sections.

Electroporation-Assisted LOXL1 Transfection in LOXL1-Deficient Mice

Once an optimized protocol for electroporation-assisted LOXL1 transfection in WT mice is established, the same protocol involving anterior chamber delivery of pDsRed2-N1 (vector control) and/or pDsRed2-N1.LOXL1 followed by electroporation will be applied in LOXL1$^{-/-}$ mice aged 8-12 w. Quantitative profiling of DSRed2 fluorescence intensity will be performed in whole mounts and immunohistochemistry sections of the TM to determine transfection efficiency, transgene localization and longevity of expression (up to 6 m after transfection). Effect of LOXL1 transfection on LOXL1 and tropoelastin expression in the TM of LOXL1$^{-/-}$ mice will be analyzed. Slit lamp and H&E staining will be used to check for the possibility of TM and anterior segment inflammation after gene delivery and electroporation.

Results and Discussion

This Example was designed to determine the utility of virus-free, electroporation-assisted transfection of the TM in live mice, as a model for therapeutic delivery of plasmid DNA comprising a therapeutic gene of interest to human subjects. The step-wise strategy will allow protocols to be optimized and will enable detection of successful transgene expression in the TM as evidenced by whole mount analysis and immunohistochemistry. Advantageously, the study design will allow for tissue localization analysis of vector and LOXL1 gene expression separately, based on the detection of different fluorophores and colocalization analysis. It is hypothesized that electroporation will increase TM transfection efficiency beyond that of anterior chamber gene perfusion delivery alone and that electrode placement and electric field vectors will influence transgene localization. Alternative plasmid DNA vectors can be tested e.g., C-instead of N-terminal gene insertion; different promoters; or plasmid DNA without fluorescent reporter, should transfection efficiency be lower than desired. Likewise, alternative plasmid DNA constructs with different fluorophores (e.g., mCherry) can be utilized if needed. TM cells are post-mitotic and transgene expression is expected to be long-lived. Variables discussed above, such as electrode positioning (e.g., limbus and posterior globe) to alter electric field vectors can be adjusted to increase expression. Electroporation at multiple locations around the TM circumference may also facilitate more widespread tissue transgene expression. If electrically-induced tissue damage occurs or TM cell viability is reduced, it may be necessary to reduce the voltage delivered. The LOXL1 gene and LOXL1-/- mice are chosen here as a model of human LOXL1 gene anomalies, which are associated with elevated IOP and exfoliation glaucoma. The present focus concerns whether electroporation enhances gene delivery to the TM to support the concept that molecular defects may be corrected in the tissue to prevent or treat disease. Subsequent to this, studies will be conducted into whether a LOXL1 transgene delivered by electroporation restores elastin maintenance and prevents development of a glaucoma phenotype in LOXL1 deficient mice.

Example 2—Naked DNA Delivery to the Trabecular Meshwork to Treat Glaucoma

Exfoliation glaucoma (XFG), a common glaucoma variant, is incurable and associated with aggressive vision loss, volatile intraocular pressure (TOP) and single nucleotide polymorphisms (SNPs) of the lysyl oxidase-like 1 (LOXL1) gene. The present example aims to identify a cure or long-term relief from XFG by correction of the molecular defects in tissues responsible for abnormal IOP.

While, viral vectors are used to efficiently deliver genes to tissues in animal models, their use for human gene therapy has been limited by immunogenic and safety risks, including fatality. Non-viral naked plasmid DNA (pDNA) does not carry these risks, however, and it is simpler to use. The systems, methods and devices disclosed herein relate to the use of pDNA as a safe and effective vector for human glaucoma gene therapy.

The trabecular meshwork (TM) is a key tissue regulator of IOP located at the exit of the anterior chamber, a location that aids gene delivery to the tissue. Genes deposited in the anterior chamber fluid must pass through the TM to exit the eye. TM cells here are phagocytic and post-mitotic, features that are expected to promote internalization of exogenous DNA and sustained transgene expression. The unique location of the TM also allows easy access for anterior chamber hydrodynamic perfusion and application of electroporation, techniques that enhance cellular uptake in vivo. As discussed above, the present application discloses effective transfected transgene expression in the TM following anterior chamber delivery of pDNA.

LOXL1 plays an important role in elastic fiber cross-linking and renewal, and is pertinent to XFG. It is unclear how known LOXL1 SNPs perturb functioning of the elastin rich TM and cause elevated IOP. In proof-of-concept studies, a pDNA vector will be used to deliver a wild-type (WT) LOXL1 gene in live LOXL1 homozygous knockout (LOXL1$^{-/-}$) mice by anterior chamber hydrodynamic perfusion. It will be determined whether it safely rescues the gene defect and alters phenotype. Parallel efficacy and safety studies will be conducted in human TM.

Efficacy of pDNA Delivery in Live Mice

The present example will evaluate the ability of pDNA-mediated LOXL1 transgene expression to rescue TM functional deficit due to impaired elastin maintenance in LOXL1-/- mice. This study will establish effectiveness of pDNA-mediated gene therapy; further the understanding of the role of LOXL1 in determining IOP and XFG.

pDNA-based WT and mutant LOXL1 genes (human SNPs: rs1048661 (R141L) and rs3825942 (G153D)) will be delivered to LOXL1-/- mice. Studies will ascertain the transfected LOXL1 proteins: (a) tissue distribution, transfection efficiency, expression duration, association with inflammation or tissue damage, and expression following electroporation. (b) Whether sustained expression affects elastic fiber organization over time. (c) effect on phenotype (clinical features, IOP, outflow facility) will be examined in LOXL1-/- mice over time.

Targeting pDNA to Human Trabecular Meshwork

This study will evaluate pDNA-based gene delivery to the human TM for human glaucoma gene therapy. It will establish efficacy and safety of pDNA-based gene delivery to the human TM and confirm applicability to humans of mouse studies. pDNA with tagged WT LOXL1 will be perfusion-delivered to the viable human TM in an ex vivo organotypic system followed by in situ 2-photon imaging to determine the transfected LOXL1 protein's: (a) distribution within the human TM, transfection efficiency, expression duration, and expression following electroporation and (b) correct co-localization with elastin, reflecting expression of a correct, efficacious and safe protein.

XFG is an attractive disease model in which to test non-viral glaucoma gene therapy devices and methods disclosed herein, for at least the following reasons: (a) XFG is common, being responsible for 25% of open angle glaucoma (OAG) worldwide; (b) XFG is more aggressive and harder to treat than primary OAG, so that finding a cure or providing effective long term relief is important; (c) strong LOXL1 SNP associations are reproducible across diverse populations, but their biologic basis is unknown and needs to be clarified; and (d) relevant mutant LOXL1 mice are available; (e) significant safety concerns remain with using viral vectors in humans and it is important to find safer alternatives.

Figure 19:
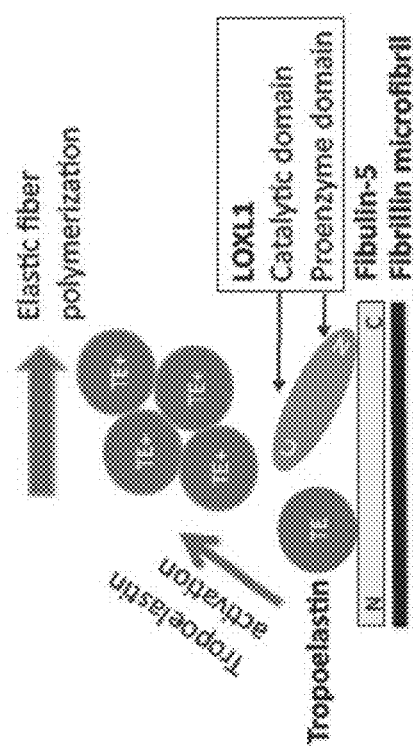
FIG. 19 is a schematic of an embodiment of elastic fiber polymerization on microfibril.

LOXL1 catalyzes elastin cross-linking and maintains elastic fibers. In XFG, evidence of elastic fiber abnormality is seen as: (a) insoluble eye deposits containing LOXL1, microfibrils and elastin epitopes; (b) spontaneous disintegration of elastic lens zonules; (c) scleral and lamina cribrosa abnormality; (d) Bruch's membrane fragility and (e) vascular abnormality causing cardiovascular and cerebrovascular disease. In what way elastic fiber abnormality contributes to IOP dysregulation is unclear but important to understand. Polymerization of tropoelastin, the monomeric form of elastin, forms elastic microfibrils on a fibrillin backbone. Fibulin-5 binds to both LOXL1 and tropoelastin, bringing them into close proximity with fibrillin (FIG. 19), so that LOXL1 co-localizes with elastin, fibrillin and fibulin-5. This allows LOXL1 to catalyze local self-assembly, stabilization and renewal of elastic microfibrils but absence or reduction of LOXL1 disrupts this process.

It is believed that LOXL1 functional insufficiency causes fault TM elastic fiber maintenance and renewal. Over time, this causes defective TM elasticity, impaired response to contractile regulatory mechanisms, and IOP elevation.

Figures 20A, 20B, 20C:
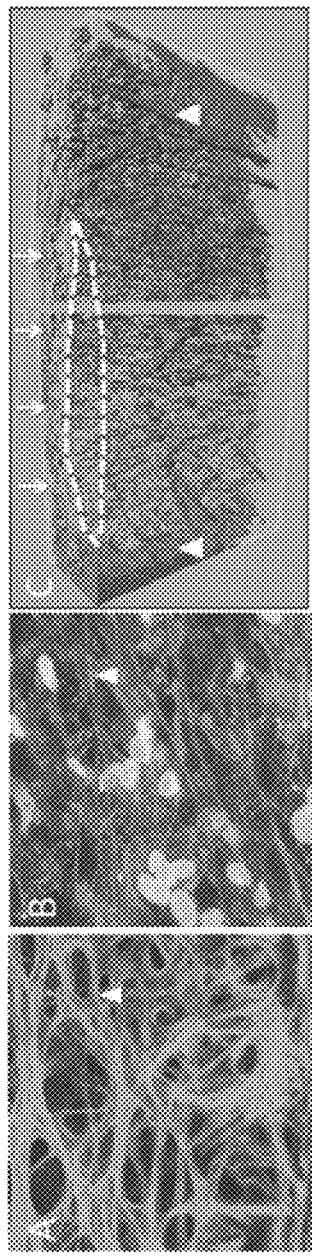
FIGS. 20A-20C depict an embodiment of elastin-rich TM.

The TM is an elastin-rich contractile tissue that drains up to 90% of aqueous from the eye. Cells in the TM regulate an intricate internal elastic fiber system and tissue contractility (FIGS. 20A-20C). FIG. 220A depicts 2-photon autofluorescence evaluation of elastic fibers surrounding the drainage pores in the TM. FIG. 20B depicts F-actin surrounding pores in the TM cells. FIG. 20C depicts a 3D model depicting the physical relationship between collagen, elastin and the location of Schlemm's Canal (dotted line). The balance wrought by regulated elastic compliance and contractile tone dynamically modulates aqueous outflow resistance and IOP. Gene expression—normal or abnormal—that influences the elasticity/contractility balance, as discussed herein, will influence outflow resistance and IOP. Thus, in XFG, aberrant cellular LOXL1 expression in the TM could compromise elastic fiber homeostasis and impair tissue compliance to contractile forces causing dysregulated outflow resistance and IOP. But resumption of normal LOXL1 expression could restore a more physiologic balance and IOP, as is the result of several methods disclosed herein.

As discussed above, the use of plasmid vectors as disclosed herein is based, at least in part, on their excellent safety profile. Immunogenicity is uncommon and should not limit the duration of transgene expression. As genomic integration is relatively inefficient, oncogenesis is anticipated to be limited. The gene packaging capacity of plasmids is significant, accommodating even large genomic DNA segments and multiple-protein coding (polycistronic expression cassettes). More recently, viral vectors such as adeno-associated viruses (AAV) have been applied to retinal gene therapy with fewer adverse events and less inflammation than vectors such as adenovirus. Still, AAV vectors retain immunogenic capacity, carry long-term risks such as oncogenesis, and cannot accommodate large genes. Other advantages of plasmids are their simple construction, easy propagation, and stability at room temperature, providing benefits for storage and handling were plasmids to be widely used clinically. pDNA has been proposed for gene delivery to organs such as liver, musculoskeletal and cardiovascular systems. Safety issues have been remarkably few in many cardiovascular clinical trials and the FDA has even approved its use in humans.

The TM is a unique tissue target for pDNA-based gene delivery. It lies at the exit for aqueous from the anterior chamber so that a gene delivered into the aqueous must encounter the TM during normal outflow. This direct path to TM cells avoids problems of systemic delivery into the blood, such as enzymatic degradation, interactions with serum components, and need to extravasate from blood vessels and migrate through ECM. However, as discussed above, other pathways of administration may also be used in some embodiments.

Plasmid delivery has been successful with other tissue compartments: corneal endothelial cells in the anterior chamber; intravenous delivery to hepatocytes within liver sinusoids; retrograde ductal delivery to salivary gland acinar cells; and injection into muscle fascial compartments to transfect muscle fibers and cells. Within isolated tissue compartments, cells are more efficiently transfected under hydrodynamic perfusion without a viral vector. In several embodiments disclosed herein, perfusion physically and transiently overcomes the plasma membrane barrier to allow exogenous DNA entry into the cytosol. By way of example, hepatocyte transfection efficiency by hydrodynamic perfusion can reach as high as 70%. Certain TM cell features such as being phagocytic may further increase the chance of transfection, as occurs with perfusion of naked siRNA. Once shuttled to the nuclei, pDNA is more likely to persist and sustain expression in post-mitotic cells such as in the TM than actively dividing cells. Expression of pDNA-mediated expression in some post-mitotic tissues lasts at least 1½ years. TM position just below the ocular surface is favorable for electroporation, a physical technique for enhancing cellular uptake. Externally, the TM lies within microns of scleral surface electrode placement. Internally, it is bathed by aqueous humor, into which pDNA is easily and minimally-invasively delivered by the transcorneal route. The aqueous physiologic salt solution is a conductive medium facilitating transmembrane voltage generation that transiently increases membrane permeability to exogenous DNA.

Figure 25:
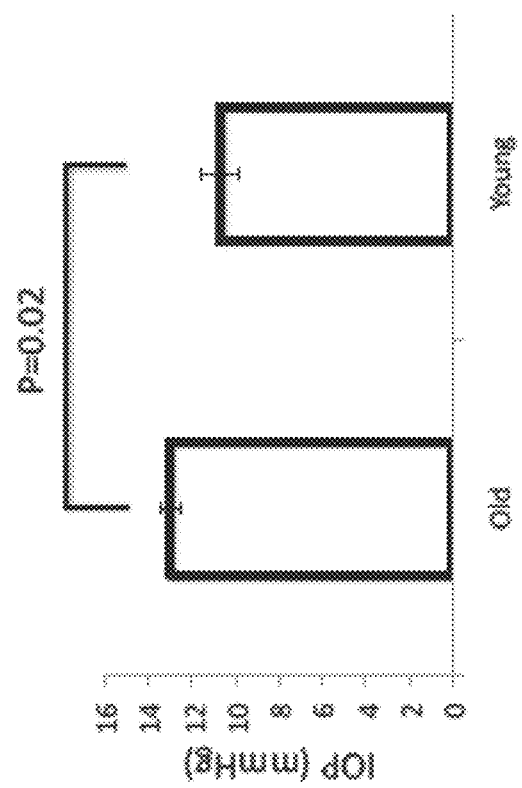
FIG. 25 is a graph of comparing embodiments of IOP in LOXL1 mice.

As discussed above, the study of glaucoma pathogenesis and therapy presents an opportunity to investigate the TM and its molecular machinery regulating aqueous outflow resistance and TOP. This platform for probing the TM permits genetic manipulation, phenotypic observation, and translational studies relevant to human glaucoma. Unlike fibrillin and fibulin-5-mutant mice that are elastin-deficient at birth, elastic fibrils in young LOXL1$^{-/-}$ mice (which are used or proposed to be used in experiments discussed herein) are normal. In older LOXL1$^{-/-}$ mice, however, poorly polymerized and immature elastin is seen instead of mature, organized elastic fibrils. Abnormalities such as organ prolapse occur due to impaired tissue support. Thus LOXL1 deficiency impairs elastin maintenance and renewal, with an abnormal phenotype developing with age. Similar stresses are placed on the elastin-rich TM, which supports physiologic TOP. While high TOP has not been reported in young LOXL1$^{-/-}$ mice, it has been determined that TOP in LOXL1$^{+/-}$ mice rises with age (FIG. 25). This scenario mimics age-related XFG, which may be preventable if LOXL1 functional insufficiency is corrected early enough. Even if TM LOXL1 aberrations are corrected later on, it may still be possible to rescue relatively physiologic elastic fiber structure and function. Effective pDNA-based gene delivery in LOXL1$^{-/-}$ mice offers a simple and effective option to test these possibilities. Also developed and disclosed herein is a human TM tissue-based model for testing pDNA delivery. Cutting-edge 2-photon excitation fluorescence imaging (TPEF) and deep tissue optical sectioning permits in situ visualization and analysis of molecular events This study focuses on whether in vivo pDNA delivery may restore loss of function due to gene defect. To that end, LOXL1$^{-/-}$ mice will receive WT and mutant forms of the LOXL1 gene by pDNA hydrodynamic perfusion in vivo, with and without electroporation. Studies are designed to (a) explore feasibility of TM pDNA transfection in vivo by characterizing transfection efficiency, expression duration, and tissue distribution; (b) determine LOXL1 transgene safety and function, as reflected in assays for inflammation, perfusion-related damage, correct ECM targeting, and possibility of elastic fiber reorganization; (c) determine if WT LOXL1 TM gene delivery in young LOXL1$^{-/-}$ mice prevents a typical LOXL1$^{-/-}$ phenotype.

pDNA comprising a gene of interest will be perfusion-delivered into the live LOXL1$^{-/-}$ mouse anterior chamber using established techniques. Initially, parameters for optimal hydrodynamic perfusion will be determined using an empty pDNA vector without LOXL1 (pCMV6-AC-GFP; OriGene cat. PS100010). After amplification and purification using an endotoxin-free plasmid prep kit, different concentrations of pDNA (0.1-1 µg/5 µl) will be perfused at flow rates commensurate with a physiologically relevant constant perfusion pressure in the range of 20-35 mmHg (though as discussed above, other pressures can also be used, depending on the embodiment). It shall be appreciated that different concentrations and/or perfusion pressures may be applicable to specific patients. Perfusion duration will be calculated to allow a volume 1-3× that of the mouse anterior chamber (~5 µL) to be delivered. Once an optimal protocol is determined, this will be used to perfuse (a) WT LOXL1 (pCMV6-AC-GFP-LOXL1; NM_005576, OriGene cat. RG209830). PBS alone or empty pDNA with GFP reporter will serve as negative controls. Viral vector with LOXL1 gene (pLenti-C-mGFP-LOXL1; OriGene cat. MR209361L2) will serve as positive controls.

Figures 21A, 21B:
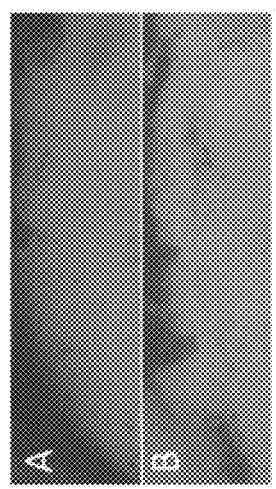
FIGS. 21A-21B depict an expression levels of plasmid DNA in the TM after hydrodynamic perfusion and after electroporation.

Electroporation will be performed once an optimal hydrodynamic perfusion protocol is determined. It will be performed using tweezer electrodes on a BTX ECM 830 electroporator (Harvard Apparatus, MA) during pDNA perfusion. Electrode tips (anode and cathode) will be placed 180 degrees apart on sclera overlying the TM, though as disclosed herein, other arrangements may readily be used. A protocol optimizing electroporation-assisted TM transfection will be determined, starting with: (a) 80V, (b) 5 pulse train with repeats, (c) 10 ms pulse duration, and (d) 100 ms pulse intervals. Tissue assays following (i) hydrodynamic delivery alone and (ii) with electroporation will be compared (FIGS. 21A-21B). FIG. 21A depicts data collected from flat mount mouse trabecular meshwork cells expressing GFP delivered by hydrodynamic perfusion only. FIG. 21B depicts enhanced GFP expression when delivery of plasmid DNA carrying the GFP gene was by perfusion combined with electroporation. Electroporation parameters can readily be fine-tuned based on findings of an individual experiment and the disclosure provided herein.

Figures 22A, 22B, 22C:
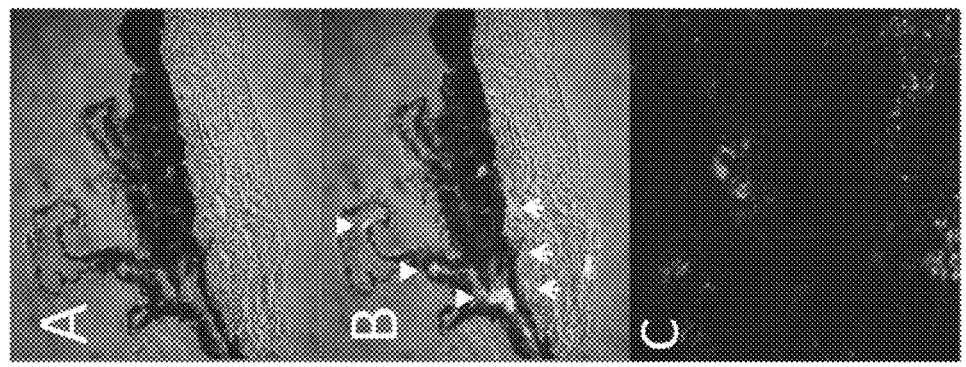
FIGS. 22A-22C depict in vivo EGFP plasmid-mediated transfection of trabecular meshwork (TM) and ciliary body (CB). 22A: Control eye, receiving vehicle only. 22B: Treated eye, receiving plasmid with reporter gene (EGFP; green expression). 22C: detail of single cells in TM with cytosolic EGFP expression. Arrows: TM. Arrowheads: CB.

1 week after pDNA delivery, animals will be euthanized and eyes enucleated for flat mount, cryosectioning and immunohistochemistry (IHC) to analyze: (1) Tissue distribution: based on GFP expression in the anterior segment tissues (e.g., TM (FIGS. 22A-22C, which depict GFP expression in mouse angle structures after plasmid perfusion delivery in a radial section (22B) compared with vehicle control (22A), with a detailed close-up of cells shown in 22C)), ciliary body, lens, cornea) and distal outflow pathways (e.g., Schlemm's canal, collector channels, episcleral vein endothelia); (2) Transfection efficiency: (i) percent TM cells bearing GFP in Hoechst-nuclear labeled MC sections; and (ii) percent TM circumference bearing GFP in anterior segment flat mount preparations; (3) Expression duration: Once repeatable transgenic protein expression is confirmed, MC will be repeated 30, 60 and 90*d* after pDNA delivery, and longer as indicated, supplemented by Western blot and quantitative PCR (qPCR) confirmation.

Figure 23:
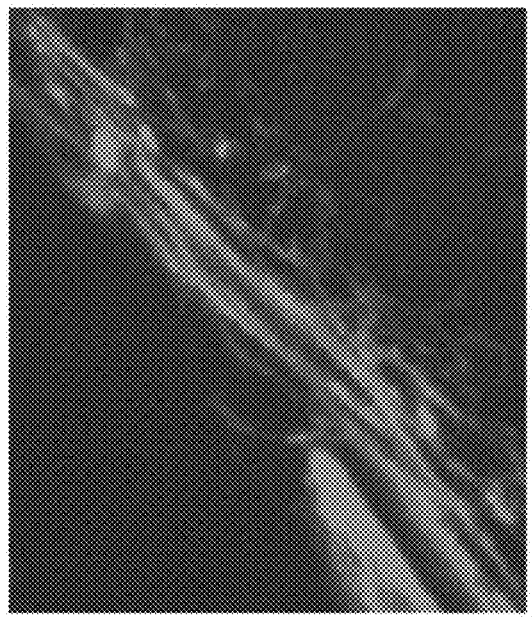
FIG. 23 depicts an embodiment of LOXL1 and tropoelastin co-localize in WT mouse TM.

To evaluate safety and effectiveness of transgene expression: (a) slit lamp examination for hyperemia and anterior chamber flare and cells will be performed; (b) perfusion-related damage will be looked for in paraffin sections following hematoxylin and eosin (H&E; structural disruption, tissue burns, inflammatory cells) and Hoechst labeling (cell loss); (c) fresh whole-eye TPEF analysis after calcein-AM labeling (cell viability analysis); (d) Bradford assay on aqueous humor samples pooled from several mice (5-10) to measure total protein as indicator of blood aqueous barrier breakdown or inflammation. The effect on elastic fiber organization will be assessed by examination of H&E sections by fluorescence microscopy to visualize and analyze elastin related eosin fluorescence by quantitative intensity analysis and Voerhoff's von Giesson staining and antibody labeled tropoelastin for comparison (see, for example FIG. 23, which shows eosin-labeled trabecular meshwork fibers).

Phenotypes will also be assessed, for example by evaluating outflow facility, resistance and responsiveness to contractility relative to percent transgene transfection, measurement of TOP, and slit lamp examination with anterior segment digital photography performed before and after pDNA delivery. Findings on duration of expression will guide longer-term observations on phenotype. Evaluations for phenotypic change will be conducted for up to 6-12 m post-pDNA delivery. As discussed above, some embodiments employ reporter elements or markers, however, in the event that such embodiments realize lower than desired efficacy, alternative approaches can be employed. For example, alternative plasmid vector designs (e.g., C- instead of N-terminal gene insertion; different promoters (e.g., MIEmCMV); and/or pDNA without fluorescent protein reporter can be used, see for example FIGS. 24A-24B). FIG. 24A depicts LOXL1 expression (using antibody labeled LOXL1-DDK, rather than GFP) amongst elastin aggregates in LOXL1-/- murine trabecular meshwork cells after plasmid DNA perfusion. FIG. 24B depicts fibrillary elastin in wild type negative control mice.

With effective pCMV6-AC-GFP-LOXL1 transgene expression, the GFP fluorescent reporter should be readily detected in the TM intracellularly and in the ECM (as evidenced by data shown in FIGS. 22 and 24), co-localized with elastin. Whereas WT elastin staining has a fibrillar pattern, LOXL1-/- elastin staining shows aggregation (FIG. 24). LOXL1-/- mice with sustained WT transgene expression may develop more of a fibrillar elastin pattern over time, reflecting elastin recovery. If transfected early enough, LOXL1-/- elastin disorganization may be prevented altogether. LOXL1 antibody labeling deficiency such as aqueous barrier breakdown and lens opacity may also be ameliorated. Antibody labeling of LOXL1 should also co-localize exclusively with transfected transgenic LOXL1 in LOXL1-/- mice, reflecting the sole presence of the transgenic LOXL1. In WT mice, however, endogenous LOXL1 should be detectable as a fraction not co-localizing with the transgenic LOXL1. Hence, endogenous and transgenic LOXL1 may be distinguished. Increasingly impaired outflow facility is expected as these mice age likely due to impaired elasticity reducing TM compliance. If WT LOXL1 expression is restored, however, a relatively physiologic response may be recovered. LOXL1-/- mice may also develop higher IOP with age (FIG. 25, which shows that intraocular pressure in heterozygous LOXL mice increases by 30% with age), in excess of that expected of WT counterparts, but restoring WT LOXL1 expression may blunt this IOP rise. Conversely, mutant LOXL1 transgene expression in LOXL1-/- mice could yield a phenotype resembling human XFG, such as insoluble immature elastin deposits in the eye that are not otherwise seen in LOXL1-/- mice. Sustained transgene expression would be needed to drive these phenotypic changes. But if transgene expression is transient or shorter than desired, alternative steps, such as those disclosed above, including but not limited to repeat pDNA delivery, or plasmid modification (e.g., inclusion of DNA nuclear-targeting sequences; reducing unmethylated CpG dinucleotide content reduces innate immunity responses. As discussed above, in one embodiment ideal expression duration is several months (e.g., 3 to 6 months). While indefinite transgene expression is enticing as a concept for cure, more finite expression is desirable to afford some control over the therapeutic process. In vivo transscleral TPEF will be applied to longitudinal studies to verify duration of transfected transgene expression. In some embodiments, TPEF findings will be validated by IHC, Western blot and qPCR.

In accordance with some embodiments, plasmids may be used as non-viral vectors to efficiently deliver genes to the human TM, offering a simple and safe option for human glaucoma gene therapy. Studies disclosed herein will establish efficiency, effectiveness and safety of pDNA-based gene delivery to the human TM ex vivo. Also provided are human tissue-based models in which the viable TM retains its original 3-dimensional structure in situ, and is imaged by TPEF deep tissue optical sectioning. In several embodiments, an artificial anterior chamber will be reconstructed for perfusion studies.

Figures 26A, 26B:
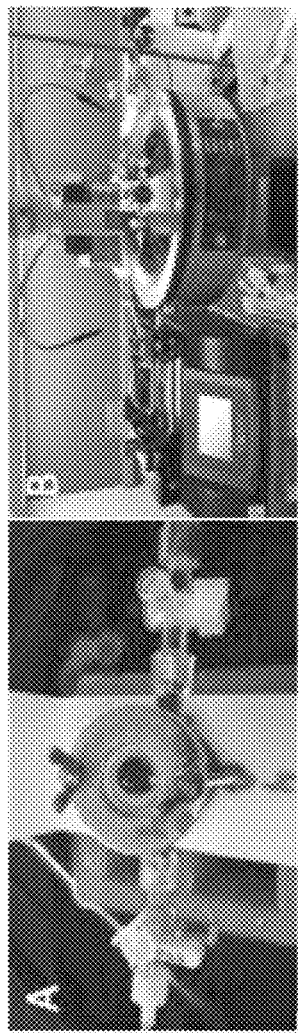
FIGS. 26A-26B depict a perfusion chamber apparatus for evaluation of delivery of plasmid DNA to human ocular tissue.

In some instances, postmortem human donor corneoscleral tissue containing the intact and viable aqueous drainage tract will be purchased from VisionShare. Initially, TPEF intravitreal imaging by an internal approach will be performed to analyze TM cell viability. For anterior chamber reconstruction, the corneoscleral rim edge will be clamped onto a base (FIG. 26A). The base has two inlets connected by inbuilt channels to luer lock hubs attached to external tubing. One inlet connects to a microsyringe pump and perfusion apparatus, the other to a pressure transducer, as shown in FIG. 26B. The perfusion apparatus will be filled with low-glucose DMEM, pH 7.4 and housed in a water jacket incubator at 37° C. with 5% CO2. pDNA will be delivered into the artificial anterior chamber with pressure and flow rate sampled in real time.

Figures 27A, 27B, 27C, 27D:
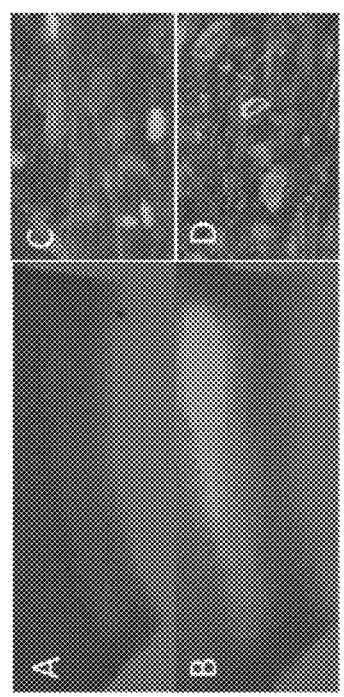
FIGS. 27A-27D depict embodiments of pDNA expression in human TM.

Hydrodynamic delivery of pDNA to human TM will be assessed as well as supplementing hydrodynamic delivery with electroporation. For example, (a) ex vivo hydrodynamic perfusion delivery will be assessed by testing and optimizing (a) empty pDNA vector, and (b) pDNA with WT LOXL1 in the human tissue-based system. These initial studies will focus on transfection efficiency and correctness, efficaciousness and safety of protein by analzing the extent to which it associates with elastin. DMEM/empty pDNA with GFP will be negative controls and pLenti-C-mGFP-LOXL1 positive controls. Also to be assessed are the, tissues after electroporationoutflow facility and resistance, except that longer term observations will be made over 7-14 d (max 28 d), combined with intravital verification of ongoing viability. Initial data indicate enhanced expression when electroporation is used to deliver plasmid DNA. Representative data is shown in FIGS. 27A-27D. FIG. 27A chose plasmid DNA expression (DSRed2) in human trabecular meshwork one week after delivery via perfusion only. FIG. 27B depicts plasmid DNA expression (also DSRed2) 180° away from the location depicted in 27A, but with electroporation being used to deliver the plasmid DNA. FIGS. 27A and 27B are matched in exposure, and the increased intensity of expression indicates a greater degree of plasmid DNA delivery when electroporation is used. FIGS. 27C and 27D depict two photon cell imaging of negative control trabecular meshwork cells.

When the singular forms "a," "an" and "the" or like terms are used herein, they will be understood to include plural referents unless the context clearly dictates otherwise. Thus, for example, reference to "an agent" includes two or more agents, and the like. The word "or" or like terms as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering histamine" include "instructing the administration of histamine." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A device for generating and applying an electrical field to an ocular target tissue, comprising:
    a first arcuate housing in which is positioned a plurality of positive electrodes;
    a second arcuate housing in which is positioned a plurality of negative electrodes,
        wherein the first arcuate housing and the second arcuate housing are configured to be coupled to form on a same plane a single ovoid-shaped structure, wherein the first and second arcuate housings are adjustable with respect to one another to adjust an outer perimeter of the single ovoid-shaped structure to a desired dimension, said desired dimension corresponding to the shape of an outer surface of an eye of a subject; and
    a control module configured to accept user input related to a percentage of the plurality of positive and negative electrodes to be activated on the single ovoid-shaped structure during the application of the electrical field to a specific ocular target tissue.

2. The device of claim 1, wherein the plurality of positive and plurality of negative electrodes are equal in number.

3. The device of claim 1, wherein the ocular target tissue is the trabecular meshwork and the electrical field is applied at a voltage between 100 mV and 100 V, wherein the electric field is pulsed between 1 and 20 pulses, wherein the pulses are applied for a duration of between 0.5 and 10 milliseconds per pulse, and wherein the pulses are separated by an interval of between about 20 to 150 milliseconds.

4. The device of claim 1, further comprising an injection system, comprising:
    a first syringe configured to deliver a therapeutic agent to an anterior chamber of the eye of the subject; and
    a second syringe configured to withdraw aqueous humor from the anterior chamber of the eye of the subject.

5. The device of claim 4, wherein the therapeutic agent comprises nucleic acid, and wherein the device is configured to deliver the therapeutic agent in a volume of about 10 to about 1000 microliters, and at a concentration between about 10 micrograms nucleic acid per milliliter to 5000 micrograms nucleic acid per milliliter.

6. The device of claim 4, wherein the volume of aqueous humor withdrawn is equivalent to the volume of therapeutic agent delivered, and the withdrawal of aqueous humor is performed prior to delivery of the therapeutic agent.

7. The device of claim 4, wherein the device is configured to deliver the therapeutic agent at a rate between about 0.1 microliters per minute and about 100 microliters per minute.

8. The device of claim 4, wherein the device is configured to deliver the therapeutic agent at a pressure between about 10 and about 40 mm of mercury.

9. The device of claim 4, wherein the therapeutic agent comprises a polynucleotide encoding lysyl oxidase-like 1 (LOXL1), CYP1B1, myocilin, TGF-beta latency-associated peptide (LAP), prostaglandin F synthase, C3 transferase, caldesmon or variants thereof.

10. The device of claim 4, further comprising a pressure transducer configured to assess an intraocular pressure of the anterior chamber.

11. The device of claim 10, wherein one or more of a volume, a concentration, a rate, a frequency, or a pressure of the delivery of the therapeutic agent is selected based on the assessed intraocular pressure.

12. The device of claim 1, wherein the first arcuate housing forms a first arcuate portion of the single ovoid-shaped structure and the second arcuate housing forms a second arcuate portion of the single ovoid-shaped structure.

13. A device for generating and applying an electrical field to an ocular target tissue, comprising:
    a first arcuate housing in which is positioned at least one positive electrode;
    a second arcuate housing in which is positioned at least one negative electrode,
        wherein the first arcuate housing and the second arcuate housing are configured to be coupled to form on a same plane a single ovoid-shaped structure, wherein the first and second arcuate housings are adjustable with respect to one another to adjust on the same plane an outer perimeter of the single ovoid-shaped structure to a desired dimension, said desired dimension corresponding to the shape of an outer surface of an eye of a subject.

14. The device of claim 13, wherein the first arcuate housing comprises a plurality of positive electrodes, and wherein the second arcuate housing comprises a plurality of negative electrodes.

15. The device of claim 14, wherein the plurality of positive and plurality of negative electrodes are equal in number.

16. The device of claim 13, further comprising a control module configured to accept user input related to a percentage of the plurality of positive and negative electrodes to be activated during the application of the electrical field to a specific ocular target tissue.

17. The device of claim 13, wherein the device is configured to apply an electrical field focused on the trabecular meshwork of the eye of the subject.

18. The device of claim 13, wherein the device is configured to apply an electrical field focused on the ciliary body of the eye of the subject.

19. The device of claim 13, wherein the device is configured to allow delivery of a therapeutic agent to a specific ocular target tissue, wherein the therapeutic agent comprises a plasmid.

20. The device of claim 13, wherein the first arcuate housing forms a first arcuate portion of the single ovoid-shaped structure and the second arcuate housing forms a second arcuate portion of the single ovoid-shaped structure.

21. A device for generating and applying an electrical field to an ocular target tissue, comprising:
   a first arcuate housing in which is positioned at least one positive electrode;
   a second arcuate housing in which is positioned at least one negative electrode,
      wherein the first arcuate housing and the second arcuate housing are configured to be coupled to form on a same plane a single ovoid-shaped structure, wherein the first and second arcuate housings are adjustable with respect to one another to adjust on the same plane an outer perimeter of the single ovoid-shaped structure to a desired dimension, said desired dimension corresponding to the shape of an outer surface of an eye of a subject; and
   an injection system for delivery of a therapeutic agent to a specific ocular target tissue for the treatment of elevated intraocular pressure.

22. The device of claim 21, wherein the therapeutic agent comprises a polynucleotide encoding lysyl oxidase-like 1 (LOXL1), CYP1B1, myocilin, TGF-beta latency-associated peptide (LAP), prostaglandin F synthase, C3 transferase, caldesmon or variants thereof.

23. The device of claim 21, wherein the first arcuate housing forms a first arcuate portion of the single ovoid-shaped structure and the second arcuate housing forms a second arcuate portion of the single ovoid-shaped structure.

* * * * *

UNITED STATES PATENT AND TRADEMARK OFFICE
CERTIFICATE OF CORRECTION

PATENT NO. : 10,117,776 B2
APPLICATION NO. : 15/335324
DATED : November 6, 2018
INVENTOR(S) : Chee Hian Tan It is certified that error appears in the above-identified patent and that said Letters Patent is hereby corrected as shown below:

In the Specification

In Column 6, Line 60, change "FIG." to --FIGS.--.

In Column 12, Line 30, change "acetytransferase," to --acetyltransferase,--.

In Column 14, Line 8, change "shape," to --shape.--.

In Column 16, Line 45, change "shape," to --shape.--.

In Column 20, Line 59, change "and or" to --and/or--.

In Column 22, Line 10, change "and or" to --and/or--.

In Column 23, Line 59, change "20 µL," to --20 µL--.

In Column 23, Line 60, change "25 µL," to --25 µL--.

In Column 23, Line 60, change "25 µL," to --25 µL--.

In Column 23, Line 61, change "30 µL," to --30 µL--.

In Column 24, Line 2, change "a the" to --the--.

In Column 25, Line 50, change "FIG." to --FIGS.--.

In Column 26, Line 51, change "(FIG." to --(FIGS.--.

In Column 27, Line 20, change "hemotoxylin" to --hematoxylin--.

Signed and Sealed this
Fifth Day of March, 2019

Andrei Iancu
*Director of the United States Patent and Trademark Office*

CERTIFICATE OF CORRECTION (continued)
U.S. Pat. No. 10,117,776 B2

In Column 30, Line 6, change "220A" to --20A--.

In Column 30, Lines 6-7, change "autofluoresence" to --autofluorescence--.

In Column 30, Line 25, change "Immunogenecity" to --Immunogenicity--.

In Column 31, Line 20, change "TOP." to --IOP.--.

In Column 31, Line 33, change "TOP." to --IOP.--.

In Column 31, Line 33, change "TOP" to --IOP--.

In Column 31, Line 34, change "TOP" to --IOP--.

In Column 31, Line 46, change "events" to --events.--.

In Column 31, Line 67, change "/5 µl)" to --/5 µL)--.

In Column 32, Line 43, change "22C))," to --(22C)),--.

In Column 32, Line 67, change "Voerhoff's von Giesson" to --Verhoeff's van Gieson--.

In Column 33, Line 6, change "TOP," to --IOP,--.

In Column 33, Line 48, change "LOXL" to --LOXL1--.

In Column 34, Line 42, change "electroporationoutflow" to --electroporation outflow--.